US006758963B1

(12) United States Patent
Hantzer et al.

(10) Patent No.: US 6,758,963 B1
(45) Date of Patent: *Jul. 6, 2004

(54) HYDROPROCESSING USING BULK GROUP VIII/GROUP VIB CATALYSTS

(75) Inventors: Slyvain S. Hantzer, Prairieville, LA (US); Kenneth Lloyd Riley, Baton Rogue, LA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/869,989

(22) PCT Filed: Jan. 14, 2000

(86) PCT No.: PCT/US00/01007

§ 371 (c)(1),
(2), (4) Date: Jul. 9, 2001

(87) PCT Pub. No.: WO00/42131

PCT Pub. Date: Jul. 20, 2000

Related U.S. Application Data

(63) Continuation-in-part of application No. 09/231,156, filed on Jan. 15, 1999, now Pat. No. 6,162,350, which is a continuation-in-part of application No. 08/900,389, filed on Jul. 15, 1997, now Pat. No. 6,156,695.

(51) Int. Cl.[7] ............................................... C10G 45/04
(52) U.S. Cl. .................. 208/213; 208/216 R; 208/108; 208/215; 208/254 H; 208/217; 208/113
(58) Field of Search ............................ 208/216 R, 108, 208/215, 254 H, 217, 213

(56) References Cited

U.S. PATENT DOCUMENTS

| 3,520,796 A | | 7/1970 | Murphy et al. ............... 208/33 |
| 4,808,563 A | * | 2/1989 | Velenyi ...................... 502/241 |
| 4,902,404 A | | 2/1990 | Ho .............................. 208/57 |
| 5,112,472 A | * | 5/1992 | Gosselink et al. ............ 208/59 |
| 5,320,741 A | * | 6/1994 | Johnson et al. ............... 208/49 |
| 5,841,013 A | | 11/1998 | Ho et al. ..................... 585/269 |
| 6,162,350 A | * | 12/2000 | Soled et al. ................ 208/113 |

FOREIGN PATENT DOCUMENTS

| EP | 0 419 266 A1 * | 3/1991 | .................... 45/16 |

OTHER PUBLICATIONS

George A. Olah, Hydrocarbon Chemistry, 1995, p. 30.*

* cited by examiner

*Primary Examiner*—Walter D. Griffin
*Assistant Examiner*—James Arnold, Jr.
(74) *Attorney, Agent, or Firm*—James H. Takemoto; George B. Georgellis; Jeremy J. Kliebert

(57) ABSTRACT

A process for preparing a lubricating oil basestock containing at least about 90% saturates. The process employs a bulk catalyst comprising at least one non-noble Group VIII metal and two Group VIB metals and wherein said metal catalyst further comprises a non-noble Group VIII molybdate in which at least a portion but less than all of molybdenum is replaced by tungsten.

20 Claims, 2 Drawing Sheets

HYDROPROCESSING USING BULK GROUP VIII/GROUP VIB CATALYSTS

CROSS REFERENCE TO RELATED APPLICATIONS

This is a continuation-in-part of U.S. Ser. No. 09/231,156 filed Jan. 15, 1999 now U.S. Pat. No. 6,162,350 which is a continuation-in-part of U.S. Ser. No. 08/900,389 filed Jul. 15, 1997 now U.S. Pat. No. 6,156,695.

FIELD OF THE INVENTION

This invention relates to the hydroprocessing of petroleum and chemical feedstocks using bulk Group VIII/Group VIB catalysts. Preferred catalysts include those comprised of Ni—Mo—W.

BACKGROUND OF THE INVENTION

As the supply of low sulfur, low nitrogen crudes decrease, refineries are processing crudes with greater sulfur and nitrogen contents at the same time that environmental regulations are mandating lower levels of these heteroatoms in products. Consequently, a need exists for increasingly efficient desulfurization and denitrogenation catalysts.

In one approach, a family of compounds, related to hydrotalcites, e.g., ammonium nickel molybdates, has been prepared. Whereas X-ray diffraction analysis has shown that hydrotalcites are composed of layered phases with positively charged sheets and exchangeable anions located in the galleries between the sheets, the related ammonium nickel molybdate phase has molybdate anions in interlayer galleries bonded to nickel oxyhydroxide sheets. See, for example, Levin, D., Soled, S. L., and Ying, J. Y., Crystal Structure of an Ammonium Nickel Molybdate prepared by Chemical Precipitation. Inorganic Chemistry, Vol. 35, No. 14, p. 4191–4197 (1996). The preparation of such materials also has been reported by Teichner and Astier, Appl. Catal. 72, 321–29 (1991); Ann. Chim. Fr. 12, 337–43 (1987), and C. R. Acad. Sci. 304 (II), #11, 563–6 (1987) and Mazzocchia, Solid State Ionics, 63–65 (1993) 731–35.

Now, when molybdenum is partially substituted for by tungsten, an amorphous phase is produced which upon decomposition and, preferably, sulfidation, provides enhanced hydrodenitrogenation (HDN) catalyst activity relative to the unsubstituted (Ni—Mo). phase.

SUMMARY OF THE INVENTION

In accordance with this invention there is provided a process for hydroprocessing a hydrocarbon feedstock, which process comprises contacting said feedstock, at hydroprocessing conditions, with a bulk catalyst comprised of at least one Group VIII metal and two Group VIB metals, which catalyst comprises a bulk metal catalyst containing non-noble Group VIII metal molybdate in which at least a portion but less than all of the molybdenum is replaced by tungsten. The hydroprocessing process is selected from at least one of hydrodesulfurization, hydrodenitrogenation, hydrodemetallation, hydrodearomatization, hydroisomerization, hydrodewaxing, hydrotreating, hydrofining and hydrocracking.

In a specific embodiment of the present invention, there is provided a process for preparing a lubricating oil basestock containing at least about 90% saturates which comprises:

(a) passing a feedstock to a hydrotreating zone containing at least one hydrotreating reactor containing a hydrotreating catalyst;

(b) hydrotreating the feedstock in the presence of the hydrotreating catalyst under hydrotreating conditions wherein the hydrotreating catalyst is a bulk metal catalyst comprising non-noble Group VIII metal molybdate in which at least a portion but less than all of molybdenum is replaced by tungsten to produce a hydrotreated feedstock; and (c) fractionating the hydrotreated feedstock.

In another embodiment of the invention, there is provided a process for preparing a lubricating oil basestock containing at least about 90% saturates which comprises:

(a) passing a feedstock to a first hydrotreating zone containing at least one hydrotreating reactor containing a first non-bulk metal hydrotreating catalyst;

(b) hydrotreating the feedstock in the presence of the first hydrotreating catalyst under first hydrotreating conditions wherein the first hydrotreating catalyst comprises at least one Group VIB and at least one non-noble Group VIII metal on a refractory oxide support to produce a first hydrotreated feedstock;

(c) passing at least a portion of the first hydrotreated feedstock to a second hydrotreating zone containing at least one hydrotreating reactor containing a second hydrotreating catalyst;

(d) hydrotreating the first hydrotreated feedstock in the second hydrotreating zone under second hydrotreating conditions wherein the second hydrotreating catalyst in said second hydrotreating zone is a bulk metal catalyst comprising non-noble Group VIII metal molybdate in which at least a portion but less than all of molybdenum is replaced by tungsten to produce a second hydrotreated feedstock;

(e) fractionating the second hydrotreated feedstock.

In yet another embodiment, there is provided a process for preparing a petroleum oil containing at least about 90% saturates which comprises:

(a) passing a feedstock to a hydrotreating zone containing at least one hydrotreating reactor containing a hydrotreating catalyst;

(b) hydrotreating the feedstock in the presence of the hydrotreating catalyst under hydrotreating conditions wherein the hydrotreating catalyst is a bulk metal catalyst comprising non-noble Group VIII metal molybdate in which at least a portion but less than all of molybdenum is replaced by tungsten to produce a hydrotreated feedstock;

(c) fractionating the hydrotreated feedstock to produce a first basestock;

(d) passing the first basestock to a hydrogenation zone containing at least one hydrogenation reactor containing a hydrogenation catalyst;

(e) hydrogenating the first basestock in the presence of the hydrogenation catalyst under hydrogenation conditions wherein the hydrogenation catalyst comprises at least one Group VIII metal; and (f) fractionating the hydrogenated product from step (e) to produce a petroleum oil containing at least about 90% saturates.

In another preferred embodiment of the present invention the catalyst composition is prepared by a process which comprises contacting the Group VIII non-noble metal component with the Group VIB metal components in the presence of a protic liquid wherein during contacting not all of the Group VIB and/or Group VIII non-noble metals are in solution.

The preferred catalyst composition of the present invention can be further described as a bulk mixed metal oxide which is preferably sulfided prior to use, and which is represented by the formula:

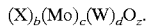

wherein X is non-noble Group VIII metal, the molar ratio of b: (c+d) is 0.5/1 to 3/1, preferably 0.75/1 to 1.5/1, more preferably 0.75/1 to 1.25/1;

The molar ratio of c:d is preferably >0.01/1, more preferably >0.1/1, still more preferably 1/10 to 10/1, still more preferably 1/3 to 3/1, most preferably substantially equimolar amounts of Mo and W, e.g., 2/3 to 3/2; and z=[2b+6(c+d)]/2.

The essentially amorphous material has a unique X-ray diffraction pattern showing crystalline peaks at d=2.53 Angstroms and d=1.70 Angstroms.

The mixed metal oxide is readily produced by the decomposition of a precursor having the formula:

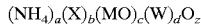

wherein the molar ratio of a:b is ≦1.0/1, preferably 0–1; and X, b, c, and d, are as defined above, and z=[a+2b+6(c+d)]/2. The precursor has similar peaks at d=2.53 and 1.70 Angstroms.

Decomposition of the precursor may be effected at elevated temperatures, e.g., temperatures of at least about 300° C., preferably about 300–450° C., in a suitable atmosphere, e.g., inerts such as nitrogen, argon, or steam, until decomposition is substantially complete, i.e., the ammonium is substantially completely driven off. Substantially complete decomposition can be readily established by thermogravimetric analysis (TGA), i.e., flattening of the weight change curve.

PREFERRED EMBODIMENTS

Figure 1:
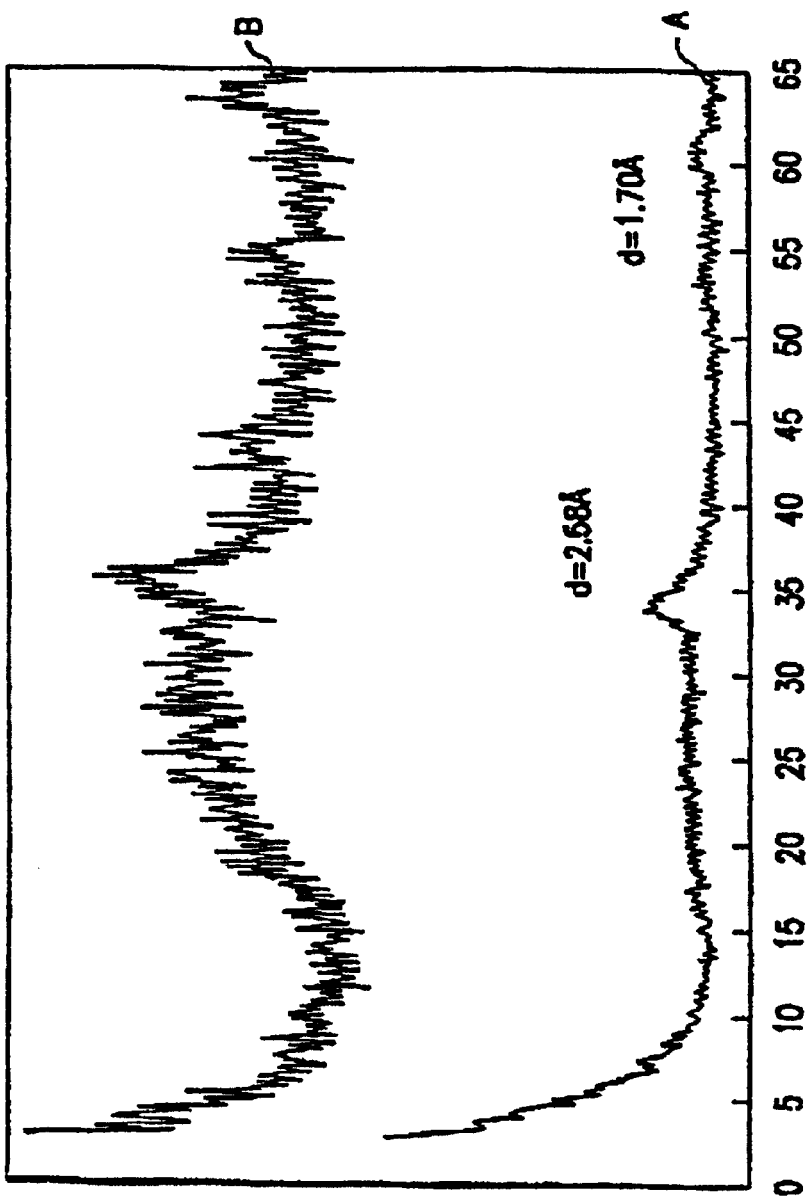
FIG. 1 is the X-ray diffraction pattern of a $NH_4Ni_{1.5}Mo_{0.5}W_{0.5}$ compound prepared by boiling precipitation before calcining (Curve A) and after calcining at 400° C. (Curve B). Note that the patterns for both the precursor and the decomposition product of the precursor are quite similar with the two peaks at essentially the same place. The ordinate is relative intensity; the abscissa is two theta (degrees).

The catalyst composition according to the invention can be used in virtually all hydroprocessing processes to treat a plurality of feeds under wide-ranging reaction conditions such as temperatures of from 200 to 450° C., hydrogen pressures of from 5 to 300 bar, liquid hourly space velocities of from 0.05 to 10 h$^{-1}$ and hydrogen treat gas rates of from 35.6 to 1780m³/m³ (200 to 10000 SCF/B). The term "hydroprocessing" encompasses all processes in which a hydrocarbon feed is reacted with hydrogen at the temperatures and pressures noted above, and include hydrogenation, hydrotreating, hydrodesulfurization, hydrodenitrogenation, hydrodemetallation, hydrodearomatization, hydroisomerization, hydrodewaxing, and hydrocracking including selective hydrocracking. Depending on the type of hydroprocessing and the reaction conditions, the products of hydroprocessing may show improved viscosities, viscosity indices, saturates content, low temperature properties, volatilities and depolarization. Feeds for hydroprocessing include reduced crudes, hydrocrackates, raffinates, hydrotreated oils, atmospheric and vacuum gas oils, coker gas oils, atmospheric and vacuum resids, deasphalted oils, dewaxed oils, slack waxes, Fischer-Tropsch waxes and mixtures thereof. It is to be understood that hydroprocessing of the present invention can be practiced in one or more reaction zones and can be practiced in either countercurrent flow or cocurrent flow mode. By countercurrent flow mode we mean a process mode wherein the feedstream flows countercurrent to the flow of hydrogen-containing treat gas.

The catalyst composition of the invention is particularly suitable for hydrotreating the hydrocarbon feeds suitable for hydroprocessing as noted above. Examples of hydrotreating include hydrogenation of unsaturates, hydrodesulfurization, hydrodenitrogenation, hydrodearomatization and mild hydrocracking. Conventional hydrotreating conditions include temperatures of from 250° to 450° C., hydrogen pressures of from 5 to 250 bar, liquid hourly space velocities of from 0.1 to 10 h$^{-1}$, and hydrogen treat gas rates of from 90 to 1780 m³/m³ (500 to 10000 SCF/B). The hydrotreating processes using the catalyst according to the invention may be particularly suitable for making lubricating oil basestocks meeting Group II or Group III base oil requirements.

A wide range of petroleum and chemical feedstocks can be hydroprocessed in accordance with the present invention. Suitable feedstocks range from the relatively light distillate fractions up to high boiling stocks such as whole crude petroleum, reduced crudes, vacuum tower residua, propane deasphalted residua, e.g., brightstock, cycle oils, FCC tower bottoms, gas oils including coker gas oils and vacuum gas oils, deasphalted residua and other heavy oils. The feedstock will normally be a $C_{10}+$ feedstock, since light oils will usually be free of significant quantities of waxy components. However, the process is also particularly useful with waxy distillate stocks, such as gas oils, kerosenes, jet fuels, lubricating oil stocks, heating oils, hydrotreated oil stock, furfural-extracted lubricating oil stock and other distillate fractions whose pour point and viscosity properties need to be maintained within certain specification limits. Lubricating oil stocks, for example, will generally boil above 230° C. and more usually above 315° C. For purposes of this invention, lubricating oil or lube oil is that part of the hydrocarbon feedstock having a boiling point of at least 315° C., as determined by ASTM D-1160 test method.

The hydrocarbon feedstocks which are typically subjected to hydrotreating herein will typically boil at a temperature above 150 C. Examples of hydrocarbon feedstocks are those derived from at least one of thermal treatment, catalytic treatment, solvent extraction, dewaxing or fractionation of a petroleum crude or fraction thereof, shale oil, tar sand or synthetic crude. If desired, the feeds can be treated in a known or conventional manner to reduce sulfur and/or nitrogen content thereof. Preferred feeds are waxy or dewaxed vacuum gas oil distillates, waxy or dewaxed hydrotreated or hydrocracked vacuum gas oil distillates and waxy or dewaxed solvent extracted raffinates boiling above 315 C.

The process of the invention is used to prepare highly saturated basestocks or other petroleum oils. These basestocks can be used to meet the requirements of Group II or Group III basestocks. The petroleum oils meet the requirements of technical or medicinal grade white oils which requirements include high saturates content and low color and toxicity. The bulk metal catalyst according to the invention may be used either alone or in combination with hydrotreating or hydrogenation catalysts. When used alone, the process for preparing a lubricating oil basestock comprises hydrotreating a feedstock in the presence of the bulk metal catalyst. The hydrotreating conditions include temperatures of from 250 to 400° C., hydrogen pressures of from 500 to 3500 psig (3549 to 24234 kPa), liquid hourly space velocities of from 0.1 to 5.0 and hydrogen treat gas rates of from 500 to 5000 scf/B (89 to 890 m$^3$/m$^3$).

The first hydrotreating zone may be followed with a hydrogenation zone. The catalyst in the hydrogenation zone may be a conventional non-bulk metal hydrotreating catalyst as described below or may contain at least one Group VIII noble metal such as platinum and/or palladium. Also included as hydrogenation catalyst are conventional bulk or non-bulk metal catalysts such as those containing nickel. The hydrogenation catalyst may be promoted with a promoter such as a halogen, e.g., chlorine or fluorine. The hydrogenation conditions include temperatures of from 150 to 400° C., hydrogen pressures of from 500 to 3500psig (3549 to 24234 kPa), liquid hourly space velocities of from 0.1 to 5.0 and hydrogen treat gas rates of from 500 to 5000 scf/B (89 to 890 m$^3$/m$^3$).

The subject catalyst may also be combined in hydrotreating processes using conventional non-bulk metal hydrotreating catalyst. In one embodiment, feedstock is first hydrotreated in a hydrotreating zone containing a non-bulk metal hydrotreating catalyst. Preferred non-bulk metal catalysts include at least one Group VIB metal such as molybdenum or tungsten and at least one non-noble metal Group VIII such as cobalt or nickel. Hydrotreating conditions include temperatures of from 250 to 400° C., hydrogen pressures of from 500 to 3500 psig (3549 to 24234 kPa), liquid hourly space velocities of from 0.1 to 5.0 and hydrogen treat gas rates of from 500 to 5000 scf/B (89 to 890 m$^3$1m$^3$). The product from the first hydrotreating zone is then hydrotreated in a second hydrotreating zone containing bulk metal catalyst according to the invention under the same hydrotreating conditions as present in the first hydrotreating zone.

The process according to the invention may be used to prepare lubricating basestocks and other petroleum oils containing saturates of at least about 90%, preferably greater than about 95%, especially greater than about 98%. Such lubricating oil basestocks meet the requirements of Group II or Group III passenger car motor oils. Highly saturated petroleum oils can be used to meet the requirements of technical and medicinal white oils. Medicinal white oils typically have greater than 99% saturates.

White mineral oils, called white oils, are colorless, transparent, oily liquids obtained by the refining of crude petroleum feedstocks. In the production of white oils, an appropriate petroleum feedstock is refined to eliminate, as completely as possible, oxygen, nitrogen, and sulfur compounds, reactive hydrocarbons including aromatics, and any other impurity which would prevent use of the resulting white oil in the pharmaceutical or food industry.

The hydrocarbon feedstocks which are typically subjected to hydrocracking herein will typically boil at a temperature above 150° C. The feedstocks can contain a substantial amount of nitrogen, e.g. at least 10 wppm nitrogen, and even greater than 500 wppm, in the form of organic nitrogen compounds. The feeds can also have a significant sulfur content, ranging from about 0.1 wt. % to 3 wt. %, or higher.

If desired, the feeds can be treated in a known or conventional manner to reduce the sulfur and/or nitrogen content thereof For purposes of the present invention where it is desirable to produce a lube basestock the feed can be a wide variety of wax-containing feedstocks including feeds derived from crude oils, shale oils and tar sands as well as synthetic feeds such as those derived from the Fischer-Tropsch process. Typical wax-containing feedstocks for the preparation of lubricating base oils have initial boiling points of about 315° C or higher, and include feeds such as reduced crudes, hydrocrackates, raffinates, hydrotreated oils, atmospheric gas oils, vacuum gas oils, coker gas oils, atmospheric and vacuum resids, deasphalted oils, slack waxes and Fischer-Tropsch wax. The feed is preferably a mixture of gas oil from a coker and vacuum distillation from conventional crudes with a maximum boiling point of the coker gas oil not to exceed 1050° F. Such feeds may be derived from distillation towers (atmospheric and vacuum), hydrocrackers, hydrotreaters and solvent extraction units, and may have wax contents of up to 50% or more.

The feedstream is contacted at hydroprocessing conditions with a bulk catalyst containing two Group VIB metal and at least one Group VIII metal, preferably two Group VIB metals and one non-noble Group VIII metal, more preferably Ni—Mo—W. The bulk catalyst compositions of the present invention can be prepared by a process wherein all of the metal precursor components are in solution or where not all of the metal components are in solution. That is, a process which comprises contacting at least one Group VIII non-noble metal component with the Group VIB metal components in the presence of a protic liquid wherein during contacting not all of the Group VIB and/or Group VIII non-noble metals are in solution.

Process for Preparing Catalyst Wherein not all of the Metals are in Solution

Generally, the contacting of the metal components in the presence of the protic liquid comprises mixing the metal components and subsequently reacting the resulting mixture. It is essential to the solid route that at least one metal components is added at least partly in the solid state during the mixing step and that the metal of at least one of the metal components which have been added at least partly in the solid state, remains at least partly in the solid state during tine mixing and reaction step. "Metal" in this context does not mean the metal in its metallic form but present in a metal compound, such as the metal component as initially applied or as present in the bulk catalyst composition.

Generally, during the mixing step either at least one metal component is added at least partly in the solid state and at least one metal component is added in the solute state, or all metal components are added at least partly in the solid state, wherein at least one of the metals of the metal components which are added at least partly in the solid state remains at least partly in the solid state during the entire process of the solid route. That a metal component is added "in the solute state" means that the whole amount of this metal component is added as a solution of this metal component in the protic liquid. That a metal component is added "at least partly in the solid state" means that at least part of the metal component is added as solid metal component and, optionally, another part of the metal component is added as a solution of this metal component in the protic liquid. A typical example is a suspension of a metal component in a protic liquid in which the metal is at least partly present as a solid, and optionally partly dissolved in the protic liquid.

If during the mixing step at least one metal component is added at least partly in the solid state and at least one metal component is added in the solute state, the following process alternatives can be applied: it is possible to first prepare a suspension of a metal component in the protic liquid and to add simultaneously, or one after the other, solutions and/or further suspensions comprising dissolved and/or suspended metal components in the protic liquid. It is also possible to first combine solutions either simultaneously or one after the other and to subsequently add further suspensions and optionally solutions either simultaneously or one after the other. If during the mixing step, each metal component is added at least partly in the solid state, it is possible to prepare suspensions comprising the metal components and to combine these suspensions either one after the other or simultaneously. It is also possible to add the metal components as such to a suspension or solution of at least one of the metal components.

In all the above-described cases, the suspension comprising a metal component can be prepared by suspending a preformed metal component in the protic liquid. However, it is also possible to prepare the suspension by (co) precipitating one or more metal components in the protic liquid. The resulting suspension can either be applied as such in the process of the solid route, i.e. further metal components either in solution, slurry or per se are added to the resulting suspension, or it can be applied after solid-liquid separation and optionally re-slurrying of the obtained solid metal component in the protic liquid.

Further, in all the above cases,: instead of a suspension of a metal component, it is also possible to use a metal component in the wetted or dry state. Wetted or dry metal components can be prepared from preformed metal components or by precipitation as described above and by subsequently partly or completely removing the protic liquid. However, care must be taken that any protic liquid is present during contacting.

It must be noted that the above process alternatives are only some examples to illustrate the mixing step. Independently from the number of metal components that are applied in the solid route, the order of addition is generally not critical to the process of this invention.

In one embodiment of the present invention (solid route), one of the metal components is added at least partly in the solid state and further metal components are added in the solute state. For instance, one metal component is added at least partly in the solid state and two metal components are added in the solute state. In another embodiment, two metal components are added at least partly in the solid state and one metal component is added in the solute state. In still another embodiment, three or more metal components are added at least partly in the solid state and no further metal components are added in the solute state. Generally, the number of metal components which are added at least partly in the solid state and which are added in the solute state is not critical to the this invention.

It will be clear that it is, e.g., not suitable to prepare first a solution comprising all metal components necessary for the preparation of a certain catalyst composition and to subsequently coprecipitate these components. Nor is it suitable for the process for the this invention to add metal components at least partly in the solid state and to choose the process conditions, such as temperature, pH or amount of protic liquid in such a way, that all added metal components are present at least at some stage completely in the solute state. On the contrary, as has been set out above, for the solid route, at least the metal of one of the metal components that are added at least partly in the solid state must remain in at least partly the solid state during the entire process of this invention.

Preferably, at least 1 wt. %, even more preferably at least 10 wt. % and most preferably at least 15 wt. % of the metal components are in the solid state during mixing, based on the total weight of all added metal components, i.e., of all metal components employed initially in the solid route, calculated as metal oxides. When it is desired to obtain a high yield, i.e., a high amount of the bulk catalyst composition, the use of metal components of which a high amount remains in the solid state during contacting is recommended. As in this case, low amounts of metal components remain solved in the mother liquid, the amount of metal components ending up in the wastewater during the subsequent solid-liquid separation is decreased.

If the metals which are added at least partly in the solid state are added as a suspension, the amount of solid metals in this suspension can be determined by filtration of the suspension at the conditions which are applied during the mixing step (temperature, pH, pressure, amount of liquid) in such a way that all solid material contained in the suspension is collected as solid filter cake. From the weight of the solid and dried filter cake, the weight of the solid metals can be determined by standard techniques. If several suspensions are applied, the weight of the solid metal components contained in these suspensions must be added to each other to give the total amount of solid metal components, calculated as metal oxides. Of course, if apart from solid metal components further solid components such as a solid binder are present in the filter cake, the weight of this solid and dried binder must be subtracted from the weight of the metal components in the solid and dried filter cake. In this case, standard techniques such as atomic absorption spectroscopy (AAS), XRF, wet chemical analysis, or ICP can determine the amount of solid metals in the filter cake.

If the metal component, which is added at least partly in the solid state, is added in the wetted or dry state, a filtration generally is not possible. In this case, the weight of the solid metal component is considered equal to the weight of the corresponding initially employed metal component. The total weight of all metal components is the amount of all metals that are initially employed as metal components, calculated as metal oxides.

It has been found that the morphology and texture of the metal component, which remains at least partly in the solid state during contacting, may determine the morphology and texture of the bulk catalyst composition. Consequently, e.g., by applying metal component particles with a certain morphology and texture, the morphology and texture of the resulting bulk catalyst particles can be controlled. "Morphology and texture" in the sense of the present invention refer to pore volume, pore size distribution, surface area, particle form, and particle size.

To obtain a bulk catalyst composition with high catalytic activity, it is therefore preferred that the metal components, which are at least partly in the solid state during contacting, are porous metal components. It is desired that the total pore volume and pore size distribution of these metal components is approximately the same as those of conventional hydrotreating catalysts. Conventional hydrotreating catalysts generally have a pore volume of 0.05–5 ml/g, preferably of 0.1–4 ml/g, more preferably of 0.1–3 ml/g and most preferably of 0.1–2 ml/g determined by nitrogen adsorption. Pores with a diameter smaller than 1 nm are generally not present in conventional hydrotreating catalysts. Further, conventional hydrotreating catalysts have generally a surface area of at least 10 $m^2$/g and more preferably of at least 50 $m^2$/g and most preferably of at least 100 $m^2$/g, determined VIB the B.E.T. method. For instance, nickel carbonate can be chosen which has a total pore volume of 0.19–0.39 ml/g and preferably of 0.24–0.35 ml/g determined by nitrogen adsorption and a surface area of 150–400 m$^2$/g and more preferably of 200–370 m$^2$/g determined by the B.E.T. method. Furthermore these metal components should have a median particle diameter of at least 50 nm, more preferably at least 100 nm, and preferably not more than 5000 μm and more preferably not more than 3000 μm. Even more preferably, the median particle diameter lies in the range of 0.1–50 μm and most preferably in the range of 0.5–50 μm. For instance, by choosing a metal component which is added at least partly in the solid state and which has a large median particle diameter, the other metal components will only react with the outer layer of the large metal component particle. In this case, so-called "core-shell" structured bulk catalyst particles are obtained.

An appropriate morphology and texture of the metal component can either be achieved by applying suitable preformed metal components or by preparing these metal components by the above-described precipitation under such conditions that a suitable morphology and texture is obtained. A proper selection of appropriate precipitation conditions can be made by routine experimentation.

As has been set out above, to retain the morphology and texture of the metal components which are added at least partly in the solid state, it is essential that the metal of the metal component at least partly remains in the solid state during the whole process of this solid route. It is noted again that it is essential that in no case should the amount of solid metals during the process of the solid route becomes zero. The presence of solid metal comprising particles can easily be detected by visual inspection at least if the diameter of the solid particles in which the metals are comprised is larger than the wavelength of visible light. Of course, methods such as quasi-elastic light scattering (QELS) or near forward scattering which are known to the skilled person can also be used to ensure that in no point in time of the process of the solid route, all metals are in the solute state.

Without wishing to be bound by any theory, it is believed that during the process of the solid route, the metal components, which are added during the mixing step at least partly, react with each other. The protic liquid is responsible for the transport of dissolved metal components. Due to this transport, the metal components come into contact with each other and can react. It is believed that this reaction can even take place if all metal components are virtually completely in the solid state. Due to the presence of the protic liquid, a small fraction of metal components may still dissolve and consequently react as described above. The presence of a protic liquid during the process of the solid route is therefore considered essential. The reaction can be monitored by any conventional technique such as IR spectroscopy, Raman spectroscopy, or by monitoring the pH of the reaction mixture.

In one preferred embodiment of the solid route, during mixing not all metal components are added completely in the solid state. Preferably, at least 0.1 wt. %, more preferably at least 0.5 wt. % and still more preferably at least 1 wt. % of the metal components initially employed in the solid route are added as a solution during the mixing step, calculated as metal oxides. In this way, proper contacting of the metal components is ensured.

The protic liquid to be applied in the solid or solution route of this invention for preparing catalyst can be any protic liquid. Examples include water, carboxylic acids, and alcohols such as methanol or ethanol. Preferably, a liquid comprising water such as mixtures of an alcohol and water and more preferably water is used as protic liquid in this solid route. Also different protic liquids can be applied simultaneously in the solid route. For instance, it is possible to add a suspension of a metal component in ethanol to an aqueous solution of another metal component. In some cases, a metal component can be used which dissolves in its own crystal water. The crystal water serves as protic liquid in this case.

The molar ratio of Group VIB to Group VIII non-noble, metals applied in the solid route ranges generally from 10:1–1:10 and preferably from 3:1–1:3. In the case of core-shell structured particles, these ratios may lie outside the above ranges. If more than one Group VIB metal is used, the ratio of the different Group VIB metals is generally not critical. The same holds when more than one Group VIII non-noble metal is used. In the case where molybdenum and tungsten are applied as Group VIB metals, the molybdenum:tungsten ratio preferably lies in the range of 9:1–1:9.

The Group VIB metal generally comprises chromium, molybdenum, tungsten, or mixtures thereof. Suitable Group VIII non-noble metals are, e.g., iron, cobalt, nickel, or mixtures thereof. Preferably, a combination of metal components comprising nickel, molybdenum and tungsten or nickel, cobalt, molybdenum and tungsten is applied in the process of the solid route. If the protic liquid is water, suitable nickel components which are at least partly in the solid state during contacting comprise water-insoluble nickel components such as nickel carbonate, nickel hydroxide, nickel phosphate, nickel phosphite, nickel formiate, nickel sulfide, nickel molybdate, nickel tungstate, nickel oxide, nickel alloys such as nickel-molybdenum alloys, Raney nickel, or mixtures thereof. Suitable molybdenum components, which are at least partly in the solid state during contacting, comprise water-insoluble molybdenum components such as molybdenum (di- and tri) oxide, molybdenum carbide, molybdenum nitride, aluminum molybdate, molybdic acid (e.g., $H_2MoO_4$), molybdenum sulfide, or mixtures thereof. Finally, suitable tungsten components which are at least partly in the solid state during contacting comprise tungsten di- and trioxide, tungsten sulfide ($WS_2$ and $WS_3$), tungsten carbide, tungstic acid (e.g., $H_2WO_4 \cdot H_2O$, $H_2W_4O_{13} \cdot 9H_2O$), tungsten nitride, aluminum tungstate (also meta-, or polytungstate) or mixtures thereof. These components are generally commercially available or can be prepared by, e.g., precipitation. e.g., nickel carbonate can be prepared from a nickel chloride, sulfate, or nirate solution by adding an appropriate amount of sodium carbonate. It is generally known to the skilled person to choose the precipitation conditions in such a way as to obtain the desired morphology and texture.

In general, metal components, which mainly contain C, O, and/or H beside the metal, are preferred because they are less detrimental to the environment. Nickel carbonate is a preferred metal component to be added at least partly in the solid state because when nickel carbonate is applied, $CO_2$ evolves and positively influences the pH of the reaction mixture. Further, due to the transformation of carbonate into $CO_2$, the carbonate does not end up in the wastewater.

Preferred nickel components which are added in the solute state are water-soluble nickel components, e.g. nickel nitrate, nickel sulfate, nickel acetate, nickel chloride, or mixtures thereof. Preferred molybdenum and tungsten components which are added in the solute state are water-soluble molybdenum and tungsten components such as alkali metal or ammonium molybdate (also peroxo-, di-, tri-, tetra-, hepta-, octa-, or tetradecamolybdate), Mo—P heteropolyanion compounds, Wo—Si heteropolyanion compounds, W—P heteropolyanion compounds, W—Si heteropolyanion compounds, Ni—Mo—W heteropolyanion compounds, Co—Mo—W heteropolyanion compounds, alkali metal or ammonium tungstates (also meta-, para-, hexa-, or polytungstate), or mixtures thereof.

Preferred combinations of metal components are nickel carbonate, tungstic acid and molybdenum oxide. Another preferred combination is nickel carbonate, ammonium dimolybdate and ammonium metatungstate. It is within the scope of the skilled person to select further suitable combinations of metal components. It must be noted that nickel carbonate always comprises a certain amount of hydroxygroups. It is preferred that the amount of hydroxy-groups present in the nickel carbonate be high.

In the following, preferred process conditions during the mixing and subsequent reaction step shall be described:

a) Mixing step:

The process conditions during the mixing step are generally not critical. It is, e.g., possible to add all components at ambient temperature at their natural pH (if a suspension or solution is applied). Generally, it is of course preferred to keep the temperature below the boiling point of the protic liquid, i.e., 100° C. in the case of water to ensure easy handling of the components during the mixing step. However, if desired also temperatures above the boiling point of the protic liquid or different pH values can be applied. If the reaction step is carried out at increased temperatures, the suspensions and solutions which are added during the mixing step are generally preheated to an increased temperature which can be equal to the reaction temperature.

b) Reaction step:

After all metal components have been mixed, they are generally agitated at a certain temperature for a certain period of time to allow the reaction to take place. The reaction point of the protic liquid such as 100° C. in the case of water the process is generally carried out at atmospheric pressure. Above this temperature, the reaction is general more preferably in the range of 3–8. As has been set out above, care must be taken that the The reaction time generally lies in the range of 1 minute to several days, more preferably 1 minute to 24 hours, and most preferably in the range of 5 minutes to 10 hours. As has been mentioned above, the reaction time depends on the temperature.

Process Step (i) According to the Solution Route

As mentioned above, alternatively to the above-described solid route for step (i), it is also possible to prepare the bulk catalyst composition by a process comprising reacting in a reaction mixture a Group VIII non-noble metal component in solution and a Group VIB metal component in solution to obtain a precipitate. As in the case of the solid route, preferably, one Group VIII non-noble metal component is reacted with two Group VIB metal components. The molar ratio of Group VIB metals to Group VIII non-noble metals applied in the process of the solution route is preferably the same as described for the solid route. Suitable Group VIB and Group VIII non-noble metal components are, e.g. those water-soluble nickel, molybdenum and tungsten components described above for the solid route. Further Group VIII non-noble metal components are, e.g., cobalt or iron components. Further Group VIB metal components are, e.g. chromium components. The metal components can be added to the reaction mixture in solution, suspension or as such. If soluble salts are added as such, they will dissolve in the reaction mixture and subsequently be precipitated.

The reaction mixture is reacted to obtain a precipitate. Precipitation is effected by adding a Group VIII non-noble metal salt solution at a temperature and pH at which the Group VIII non-noble metal and the Group VIB metal precipitate, adding a compound which complexes the metals and releases the metals for precipitation upon temperature increase or pH change or adding a Group VIB metal salt solution at a temperature and pH at which the Group VIII non-noble metal and Group VIB metal precipitate, changing the temperature, changing the pH, or lowering the amount of the solvent. The precipitate obtained with this process appears to have high catalytic activity. In contrast to the conventional hydroprocessing catalysts, which usually comprise a carrier impregnated with Group VIII non-noble metals and Group VIB metals, said precipitate can be used without a support. Unsupported catalyst compositions are usually referred to as bulk catalysts. Changing the pH can be done by adding base or acid to the reaction mixture, or adding compounds, which decompose upon temperature, increase into hydroxide ions or $H^+$ ions that respectively increase or decrease the pH. Examples of compounds that decompose upon temperature increase and thereby Increase or decrease the pH are urea, nitrites, ammonium cyanate, ammonium hydroxide, and ammonium carbonate.

In an illustrative process according to the solution route, solutions of ammonium salts of a Group VIB metal are made and a solution of a Group VIII non-noble metal nitrate is made. Both solutions are heated to a temperature of approximately 90° C. Ammonium hydroxide is added to the Group VIB metal solution. The Group VIII non-noble, metal solution is added to the Group VIB metal solution and direct precipitation of the Group VIB and Group VIII non-noble metal components occurs. This process can also be conducted at lower temperature and/or decreased pressure or higher temperature and/or increased pressure.

In another illustrative process according to the solution route, a Group VIB metal salt, a Group VIII metal salt, and ammonium hydroxide are mixed in solution together and heated so that ammonia is driven off and the pH is lowered to a pH at which precipitation occurs. For instance when nickel, molybdenum, and tungsten components are applied, precipitation typically occurs at a pH below 7.

Independently from whether the solid or solution route is chosen in step (i),the resulting bulk catalyst composition preferably comprises and more preferably consists essentially of bulk catalyst particles having the characteristics of the bulk catalyst particles described under the heading "Catalyst compositions of the invention."

The bulk catalyst composition of step (i) can generally be directly shaped into hydroprocessing particles. If the amount of liquid of the bulk catalyst composition resulting from step (i) is so high that it cannot be directly subjected to a shaping step, a solid liquid separation can be performed before shaping. Optionally the bulk catalyst composition, either as such or after solid liquid separation, can be calcined before shaping.

Process Step (ii)

It is preferred to add a binder material during the process of the invention. More in particular, a binder material can be added during the preparation of the bulk catalyst composition and/or the bulk catalyst composition can be composited with a binder material before the shaping step. The latter alternative is generally preferred. The binder material can be added in the dry state, either calcined or not, in the wetted and/or suspended state and/or as solution. As has been mentioned above, "binder material" in the sense of the present invention refers to a binder and/or a precursor thereof.

If the binder material is added during the preparation of the bulk catalyst composition, the following options are available: If, e g., the bulk catalyst composition in step (i) is prepared according to the solid route, the metal components can be added to the binder material either simultaneously or one after the other. Alternatively, the metal components can be combined as described above and subsequently a binder material can be added to the combined metal components. It is further possible to combine part of the metal components either simultaneously or one after the other, to subsequently add the binder material and to finally add the rest of the metal components either simultaneously or one after the other. For instance, the metal component which is at least partly in the solid state during contacting can be first mixed and if desired shaped with the binder material and subsequently, further metal components can be added to the optionally shaped mixture. However, it is also possible to combine the binder with metal components in the solute state and to subsequently add a metal component at least partly in the solid state. Finally, simultaneous addition of the metal components and the binder material is possible. Moreover, the binder material can be added during the reaction step of the solid route in step (i).

If the solution route is applied in step (i), the binder material can be added to the reaction mixture either in combination or not with one or more of the metal components before or after precipitation.

If the binder material is added as a solution, care must be taken that the binder will be converted into the solid state during the process of the invention. This can be done by adjusting the pH conditions during step (i) in such a way that precipitation of the binder occurs. Suitable conditions for the precipitation of the binder are known to the skilled person and need no further explanation. If the amount of liquid of the resulting bulk catalyst—binder composition is too high, optionally a solid liquid separation can be carried out. Following the preparation of the bulk catalyst—hinder composition and optional solid liquid separation, the bulk catalyst—binder composition can be shaped directly. Optionally, the bulk catalyst—binder composition can be calcined and subsequently re-wetted prior to shaping. This is especially preferred in the case where the bulk catalyst composition has been prepared VIB the solution route using nitrate and/or ammonium salts. Moreover, additional binder material can be added subsequent to the preparation of the above bulk catalyst binder composition.

As has been set out above, it is preferred to first prepare the bulk catalyst composition and to subsequently composite the resulting bulk catalyst composition with the binder material. Optionally, the bulk catalyst composition can be subjected to a solid-liquid separation before being composited with the binder material. After solid-liquid separation, optionally, a washing step can be included. Further, it is possible to calcine the bulk catalyst composition after an optional solid liquid separation and drying step and prior to compositing it with the binder material.

In all the above-described process alternatives, the term "compositing the bulk catalyst composition with a binder material" means that the binder material is added to the bulk catalyst composition or vice versa and the resulting composition is mixed.

As has been set out above, the median diameter of the bulk catalyst particles is at least 50 nm, more preferably at least, 100 nm, and preferably not more than 5000 μn and more preferably not more than 3000 μm. Even more preferably, the median particle diameter lies in the range of 0.1–50 m and most preferably in the range of 0.5–50 μμm.

Binder materials to be applied in the process of the invention may be any materials that are conventionally applied as a binder in hydroprocessing catalysts. Examples include silica, silica-alumina, such as conventional silica-alumina, silica-coated alumina and alumina-coated silica, alumina such as (pseudo) boehmite, or gibbsite, titania, zirconia, cationic clays or anionic clays such as saponite, bentonite, kaoline, sepiolite or hydrotalcite, or mixtures thereof. Preferred binders are silica, silica-alumina, alumina, titanic, zirconia, or mixtures thereof. These binders may be applied as such or after peptization. It is also possible to apply precursors of these binders that, during the process of the invention are converted into any of the above-described binders. Suitable precursors are, e g., alkali metal aluminates (to obtain an alumina binder), water glass (to obtain a silica binder), a mixture of alkali metal aluminates and water glass (to obtain a silica alumina binder), a mixture of sources of a di-, tri-, and/or tetravalent metal such as a mixture of water-soluble salts of magnesium, aluminum and/or silicon (to prepare a cationic clay and/or anionic clay), chlorohydrol, aluminum sulfate, or mixtures thereof.

If desired, the binder material may be composited with a Group VIB metal and/or a Group VIII non-noble metal, prior to being composited with the bulk catalyst composition and/or prior to being added during the preparation thereof. Compositing the binder material with any of these metals may be carried out by impregnation of the solid binder with these materials. The person skilled in the art knows suitable impregnation techniques. If the binder is peptized, it is also possible to carry out the peptization in the presence of Group VIB and/or Group VIII non-noble metal components.

If alumina is applied as binder, the surface area preferably lies in the range of 100–400 $m^2/g$, and more preferably 150–350 $m^2/g$, measured by the B.E.T. method. The pore volume of the alumina is preferably in the range of 0.5–1.5 ml/g measured by nitrogen adsorption.

Generally, the binder material to be added in the process of the invention has less catalytic activity than the bulk catalyst composition or no catalytic activity at all. Consequently, by adding a binder material, the activity of the bulk catalyst composition may be reduced. Therefore, the amount of binder material to be added in the process of the invention generally depends on the desired activity of the final catalyst composition. Binder amounts from 0–95 wt. % of the total composition can be suitable, depending on the envisaged catalytic application. However, to take advantage of the resulting unusual high activity of the composition of the present invention, binder amounts to be added are generally in the range of 0.5–75 wt. % of the total composition.

If in the process of the invention, a binder material is used, the resulting catalyst composition comprises the bulk catalyst particles obtained in step (i) imbedded in the binder material. In other words, during the process of the invention, the bulk catalyst particles generally do not disintegrate but normally, the morphology of the bulk catalyst particles is essentially maintained in the resulting catalyst composition.

Process Step (iii)

The catalyst composition resulting from the above-described process alternatives can be directly shaped. Shaping comprises extrusion, pelletizing, beading, and/or spray drying. It must be noted that if the catalyst composition is to be applied in slurry type reactors, fluidized beds, moving beds, expanded beds, or ebullating beds, spray drying or beading is generally applied for fixed bed applications, generally, the catalyst composition is extruded, pelletized and/or beaded. In the latter case, prior to or during the shaping step, any additives that are conventionally used to facilitate shaping can be added. These additives may comprise aluminum stearate, surfactants, graphite or mixtures thereof. These additives can be added at any stage prior to the shaping step. Further, when alumina is used as a binder, it may be desirable to add acids prior to the shaping step such as nitric acid to increase the mechanical strength of the extrudates.

It is preferred that a binder material is added prior to the shaping step. Further, it is preferred that the shaping step is carried out in the presence of a liquid, such as water. Preferably, the amount of liquid in the extrusion mixture, expressed as LOI is in the range of 20–80%

The resulting shaped catalyst composition can, after an optional drying step, be optionally calcined. Calcination however is not essential to the process of the invention. If a calcination is carried out in the process of the invention, it can be done at a temperature of, e.g., from 100°–600° C. and preferably 350° to 500° C. for a time varying from 05 to 48 hours. The drying of the shaped particles is generally carried out at temperatures above 100° C.

Additional Process Steps:

In a preferred embodiment of the invention, the catalyst composition is subjected to spray drying, (flash) drying, milling, kneading, or combinations thereof prior to shaping. These additional process steps can be conducted either before or after a binder is added, after solid-liquid separation, before or after calcination and subsequent to re-wetting. It is believed that by applying any of the above-described techniques of spray drying, (flash) drying, milling, kneading, or combinations thereof, the degree of mixing between the bulk catalyst composition and the binder material is improved. This applies to both cases where the binder material is added before or after the application of any of the above-described methods. However, it is generally preferred to add the binder material prior to spray drying and/or any alternative technique. If the binder is added subsequent to spray drying and/or any alternative technique, the resulting composition is preferably thoroughly mixed by any conventional technique prior to shaping. An advantage of, e.g., spray drying is that no wastewater streams are obtained when this technique is applied.

It must be noted that combinations of the above-described processes with respect to the binder addition can be applied. For instance, part of the binder material can be added during the preparation of the bulk catalyst composition and part of the binder material can be added at any subsequent stage prior to shaping. Further, it is also possible to apply more than one of the above-described techniques.

In all the above process steps the amount of liquid must be controlled. If, e.g., prior to subjecting the catalyst composition to spray drying, the amount of liquid is too low, additional liquid must be added. If, on the other hand, e.g. prior to extrusion of the catalyst composition, the amount of liquid is too high, the amount of liquid must be reduced by, e.g., solid liquid separation via, e.g., filtration, decantation, or evaporation and, if necessary, the resulting material can be dried and subsequently be re-wetted to a certain amount. For all the above process steps, it is within the scope of the skilled person to control the amount of liquid appropriately. Generally, it may be preferred to choose the amount of liquid during the process steps (i) and (ii) in such a way that no additional drying step is necessary prior to applying spray drying and/or any alternative technique or shaping. Further, it is preferred to carry out any of the above techniques in such a way that the resulting, e.g., spray dried and/or kneaded composition contains an amount of liquid which allows the composition to be directly shaped. Spray drying is preferably carried out at an outlet temperature in the range of 100°–200° C. and more preferably 120°–180° C.

Apart from the binder materials described above, it is also possible to add conventional hydrodenitrogenation catalysts. These catalysts can be added in the spent, regenerated, or fresh state. In principle, it is hydroprocessing catalysts such as conventional hydrodesulfurization and possible to add these catalysts instead of a binder material or precursor thereof. In other words, it is possible to carry out all the abovedescribed process alternatives wherein the binder material or precursor thereof is replaced fully or in part by a conventional hydroprocessing catalyst. In principle, the conventional hydroprocessing catalyst can be added at any stage of the process of the present invention prior to the shaping step. Within the context of this description, "at any stage of the process prior to the shaping step" means: it can be added during the preparation of the bulk catalyst composition, and/or subsequent to the preparation of the bulk catalyst composition but prior to the addition of the binder material, and/or during, and/or subsequent to the addition of the binder material, but prior to spray dying or any alternative method, and/or during and/or subsequent to spray drying or any alternative method but prior to the shaping step it is possible to add a conventional hydroprocessing catalyst during the compositing step (ii) with the binder If desired, the conventional hydroprocessing catalyst may be milled before 10 being applied in the process of the invention.

Furthermore, a cracking component may be added during the process of the present invention. A cracking component in the sense of the present invention is any conventional cracking component such as cationic clays, anionic clays, zeolites such as ZSM-5, (ultra-stable) zeolite Y, zeolite X, ALPO's, SAPO's, amorphous cracking components such as silica-alumina, or mixtures thereof. It will be clear that some materials may act as a binder and a cracking component at the same time. For instance, silica-alumina may have at the same time a cracking and a binding function.

If desired, the cracking component may be composited with a Group VIB metal and/or a Group VIII non-noble metal prior to being composited with the bulk catalyst composition and/or prior to being added during the preparation thereof. Compositing the cracking component with any of these metals may be carried out by impregnation of the cracking component with these materials.

The cracking component can be added at any stage of the process of the present invention prior to the shaping step. However, it is preferred to add the cracking component during the compositing step (ii) with the binder.

Generally, it depends on the envisaged catalytic application of the final catalyst composition which of the above-described cracking components is added. A zeolite is preferably added if the resulting composition shall be applied in hydrocracking or fluid catalytic cracking. Other cracking components such as silica-alumina or cationic clays are preferably added if the final catalyst composition shall be used in hydrotreating applications. The amount of cracking material that is added depends on the desired activity of the final composition and the application envisaged and thus may vary from 0–80 wt. %, based on the total weight of the catalyst composition.

If desired, further materials can be added in addition to the metal components already added in step (i). These materials include any material that is added during conventional hydroprocessing catalyst preparation. Suitable examples are phosphorus compounds, borium compounds, fluor-containing compounds, additional transition metals, rare earth metals, fillers, or mixtures thereof.

Suitable phosphorus compounds include ammonium phosphate, phosphoric acid, or organic phosphorus compounds. Phosphorus compounds can be added at any stage of the process of the present invention prior to the shaping step and/or subsequent to the shaping step. If the binder material is peptized, phosphorus compounds can also be used for peptization. For instance, the binder can be peptized by contacting the binder with phosphoric acid or with a mixture of phosphoric and nitric acid.

Suitable additional transition metals are, e.g., rhenium, ruthenium, rhodium, iridium, chromium, vanadium, iron, cobalt, platinum, palladium, cobalt, nickel, molybdenum, or tungsten. Nickel, molybdenum, and tungsten can be applied in the form of any of the water-insoluble nickel, molybdenum and/or tungsten components that are described above for the solid route. These metals can be added at any stage of the process of the present invention prior to the shaping step. Apart from adding these metals during the process of the invention, it is also possible to composite the final catalyst composition therewith. It is, e.g., possible to impregnate the final catalyst composition with an impregnation solution comprising any of these metals.

The processes of the present invention for preparing the bulk catalyst compositions may further comprise a sulfidation step. Sulfidation is generally carried out by contacting the catalyst composition or precursors thereof with a sulfur containing compound such as elementary sulfur, hydrogen sulfide or polysulfides. The sulfidation can generally be carried out subsequently to the preparation of the bulk catalyst composition but prior to the addition of a binder material, and/or subsequently to the addition of the binder material but prior to subjecting the catalyst composition to spray drying and/or any alternative method, and/or subsequently to subjecting the composition to spray drying and/or any alternative method but prior to shaping, and/or subsequently to shaping the catalyst composition. It is preferred that the sulfidation is not carried out prior to any process step that reverts the obtained metal sulfides into their oxides. Such process steps are, e.g., calcination or spray drying or any other high temperature treatment in the presence of oxygen. Consequently, if the catalyst composition is subjected to spray drying and/or any alternative technique, the sulfidation should be carried out subsequent to the application of any of these methods. Additionally to, or instead of, a sulfidation step, the bulk catalyst composition may be prepared from at least one metal sulfide. If, e.g., the solid route is applied in step (i), the bulk catalyst component can be prepared form nickel sulfide and/or molybdenum sulfide and/or tungsten sulfide.

If the catalyst composition is used in a fixed bed processes, the sulfidation is preferably carried out subsequent to the shaping step and, if applied, subsequent to the last calcination step. Preferably, the sulfidation is carried outer situ, i.e., the sulfidation is carried out in a separate reactor prior to loading the sulfided catalyst composition into the hydroprocessing unit. Furthermore, it is preferred that the catalyst composition is both sulfided ex situ and in situ.

Catalyst Compositions of this Invention

The present invention further refers to catalyst compositions obtainable by any of the above-described processes. Furthermore, the present invention pertains to a catalyst composition comprising bulk catalyst particles wherein the bulls catalyst particles comprise 30–100 wt. % of at least one Group VIII non-noble metal and at least one Group VIB metal, based on the total weight of the bulk catalyst particles, calculated as metal oxides and wherein the bulk catalyst particles have a surface area of at least 10 $m^2/g$. Catalyst compositions comprising bulk catalyst particles comprising one Group VIII non-noble metal and two Group VIB metals are preferred. It has been found that in this case, the bulk catalyst particles are sintering-resistant. Thus the active surface area of the bulk catalyst particles is maintained during use. The molar ratio of Group VIB to Group VIII non-noble metals ranges generally from 10:1–1:10 and preferably from 3:1–1:3. In the case of a core-shell structured particle, these ratios of course apply to the metals contained in the shell. If more than one Group VIB metal is contained in the bulk catalyst particles, the ratio of the different Group VIB metals is generally not critical. The same holds when more than one Group VIII non-noble metal is applied. In the case where molybdenum and tungsten are present as Group VIB metals, the molybdenum:tungsten ratio preferably lies in the range of 9:1–1:9. Preferably the Group VIII non-noble metal comprises nickel and/or cobalt. It is further preferred that the Group VIB metal comprises a combination of molybdenum and tungsten. Preferably, combinations of nickel/molybdenum/tungsten and cobalt/molybdenum/tungsten and nickel/cobalt/molybdenum/tungsten are used. These types of precipitates appear to be sinter-resistant. Thus, the active surface area of the precipitate is remained during use.

The metals are preferably present as oxidic compounds of the corresponding metals, or if the catalyst composition has been sulfided, sulfidic compounds of the corresponding metals.

In the following the bulk catalyst particles (in the following designated as "particles") which are present in the catalyst composition of the present invention will be described in more detail:

Preferably the particles have a surface area of at least 50 $m^2/g$ and more preferably of at least 100 $m^2/g$ measured VIB the B.E.T. method. It is furthermore preferred that the particles comprise 50–100 wt. %, and even more preferably 70–100 wt. % of at least one Group VIII non-noble metal and at least one Group VIB metal, based on the total weight of the particles, calculated as metal oxides. The amount of Group VIB and Group VIII non-noble metals can easily be determined VIB TEM-EDX.

It is desired that the pore size distribution of the particles is approximately the same as the one of conventional hydrotreating catalysts. More in particular, these particles have preferably a pore volume of 0.05–5 ml/g, more preferably of 0.1–4 ml/g, still more preferably of 0.1–3 ml/g and most preferably 0.1–2 ml/g determined by nitrogen adsorption. Preferably, pores smaller than 1 nm are not present. Furthermore these particles preferably have a median diameter of at least 50 nm, more preferably at least 100 nm, and preferably not more than 5000 $\mu$m and more preferably not more than 3000 $\mu$m. Even more preferably, the median particle diameter lies in the range of 0.1–50 $\mu$m and most preferably in the range of 05–50 $\mu$m.

It was found that the bulk catalyst particles have a characteristic X-ray diffraction pattern which differs from catalysts obtained by co-mixing and conventional hydroprocessing catalysts obtained by impregnation. The X-ray diffraction pattern of the bulk catalyst particles comprises, and preferably essentially consists of, peaks characteristic to the reacted metal components. If, e.g., nickel hydroxy-carbonate has been contacted with a molybdenum and tungsten component as described above, the resulting bulk catalyst particles are characterized by an X-ray diffraction pattern which comprises peaks at d values of (4.09), 2.83, 2.54, 2.32, 2.23, 1.71, (1.54), 1.47. Values in brackets indicate that the corresponding peaks are rather broad and/or have a low intensity or are not distinguished at all. The term "the X-ray diffraction pattern essentially consists of " these peaks means that apart from these peaks, there are essentially no further peaks contained in the diffraction pattern. The precipitate for catalyst obtained by the solution route has a characteristic X-ray diffraction pattern which differs from catalyst obtained by co-mixing and conventional hydroprocessing catalysts obtained by impregnation. For instance the X-ray diffraction pattern of a Ni—Mo—W precipitate as prepared by the solution route has peaks at d values of 2.52, 1.72 and 1.46.

Generally, it is possible to perform the above-described process in such a way to obtain bulk catalyst particles characterized by an X-ray diffraction pattern that does contain virtually no peak characteristic to the metal components applied in this process as starting materials. Of course, if desired, it is also possible to choose the amounts of metal components in such a way as to obtain bulk catalyst particles characterized by an X-ray diffraction pattern still comprising one or more peaks characteristic to at least one of these metal components. If, e.g., a high amount of the metal component which is at least partly in the solid state during contacting is added, or if this metal component is added in the form of large particles, small amounts of this metal component may be traced in the X-ray diffraction pattern of the resulting bulk catalyst particles.

Generally, if the solid route is applied, at least one of the metals is anisotropically distributed in the particles. The metal of the metal component that is at least partly in the solid state during the solid route is generally concentrated in the inner part, i.e., the core of the final particles. Generally, the concentration of this metal in the outer part, i.e. the shell of the particle is at most 95% and in most cases at most 90% of the concentration of this metal in the core of the particles. Further, it has been found that the metal of a metal component that is applied in the solute state during the solid route is also anisotropically distributed in the particles. More in particular, the concentration of this metal in the core of the particles is generally lower than the concentration of this metal in the shell. Still more in particular, the concentration of this metal in the core of the particles is at most 80% and frequently at most 65% and often at most 50% of the concentration of this metal in the shell. It must be noted that the above-described anisotropic metal distributions can be found in the composition of the invention, independently upon whether the composition has been calcined or not and/or sulfided.

In the above cases, the shell has generally a thickness of 50–1000 nm and preferably of 100–500 nm. The amount of these particles in the catalyst composition of the invention preferably lies in the range of 5–100 wt. %, based on the total weight of the catalyst composition.

As previously been mentioned, the catalyst composition comprises additionally a suitable binder material. Suitable binder materials are preferably those described above. The particles are embedded in the binder material that functions as glue to hold the particles together. Preferably, the particles are homogeneously distributed within the binder. The presence of the binder thus leads generally to an increased mechanical strength of the final catalyst composition. Generally, the catalyst composition of the invention has a mechanical strength, expressed as side crush strength of at least 1 lb./mm and preferably of at least 3 lb./mm (measured at extrudates with a diameter of 1–2 mm). The binder material generally contains 0–90 wt. % of the Group VIB and Group VIII non-noble metals which are also contained in the particles. The binder material generally even contains these metals if it has not been composited with any of these metals prior to being combined with the bulk catalyst composition of step (i).

The amount of binder depends on the desired activity of the catalyst composition. Binder amounts from 0–95 wt. % of the total composition can be suitable, depending on the envisaged catalytic application. However, to take advantage of the unusual high activity of the composition of the present invention, binder amounts are generally in the range of 0.5–75 wt. % of the total composition.

If desired, the catalyst composition may comprise a suitable cracking component. Suitable cracking components are preferably those described above. The amount of the cracking component is preferably in the range of 0–80 wt. %, based on the total weight of the catalyst composition.

Also as previously stated, the catalyst composition may comprise conventional hydroprocessing catalysts. The binder materials and cracking components of the conventional hydroprocessing catalyst generally comprise any of the above-described binder materials and cracking components. The hydrogenation metals of the conventional hydroprocessing catalyst generally comprise Group VIB and Group VIII non-noble metals such as combinations of nickel or cobalt with molybdenum or tungsten. Suitable conventional hydroprocessing catalysts are, e.g., hydrotreating catalysts, These catalysts can be in the spent, regenerated, or fresh state.

Furthermore, the catalyst composition may comprise any compound that is conventionally present in hydroprocessing catalysts such as phosphorus compounds, additional transition metals, rare earth metals, or mixtures thereof. Suitable additional transition metals are, e.g. rhenium, ruthenium, rhodium, iridium, chromium, vanadium, iron, cobalt, platinum, palladium, cobalt, nickel molybdenum, or tungsten. All these metal compounds generally are present in the oxidic form if the catalyst composition has been calcined and/or in the sulfided form if the catalyst composition has been sulfided.

The surface area of the catalyst composition preferably is at least 40 $m^2/g$, more preferably at least 80 $m^2/g$ and most preferably at least 120 $m^2/g$. The total pore volume of the catalyst composition is preferably at least 0.05 ml/g and more preferably at least 01 ml/g as determined by water porosimetry. To obtain catalyst compositions with high mechanical strength, it may be desirable that the catalyst composition of the invention has a low macroporosity.

Characterization Methods

1. Side Crush Strength Determination

First, the length of, e.g., an extrudate particle is measured, and then the extrudate particle is subjected to compressive loading by a movable piston. The force kit required to crush the particle is measured. The procedure is repeated with at least 40 extrudate particles and the average is calculated as force (lbs.) per unit length (mm).

2. Water Porosimetry

The pore volume of a sample is determined by filling the pore space to saturation with water. The quantity of water is determined by its volume added or the weight increase of the sample. The pores space can be filled by incrementally adding water from a burette to the sample, with vigorous shaking after each addition, until the first sign of wetness at the outside of the sample appears. Another possibility is to saturate the sample contained in a tube fitted with a porous bottom with water in an ultrasound bath. The excess water (the water not residing in the pores) is removed VIB centrifugation and the difference in the dry and saturated catalyst weights is then used to determine the total water uptake. From this, the pore volume is calculated.

3. Determination of the Lose on Ignition (LOI)

A sample is mixed well to prevent inhomogeneity. The weighed and mixed sample is transferred to a preheated and weighed crucible. The crucible is then put in a drying oven or cold muffle furnace and the temperature is increased. The sample is dried or ignated at this temperature for one hour. The crucible containing the dried or ignated sample is cooled in a desiccator and weighed again.

The LOI is determined according to the following formula $$\% \, LOI = \frac{(b-c)}{a} \times 100$$

where a is weight of the sample (in gram), b is the mass of the crucible and the sample before drying and/or ignition (in gram), and c is the weight of the crucible and the sample after drying and/or ignition (in gram).

In the process according to the present invention, a Group VIII non-noble metal-containing compound in solution and a Group VIB metal-containing compound in solution are reacted. Thus, the metal compounds are in the solute state when reacted to obtain a precipitate. The Group VIII non-noble metal-containing compound and the Group VIB metal-containing compound may be in solution when added to the reaction mixture or else will become dissolved when present in the reaction mixture. In the latter case, the metals are actively dissolved in the reaction mixture, for instance by stirring, increasing the amount of solvent, changing the temperature, changing the pressure, or changing the pH. The metals may be dissolved in any protic liquid such as water, carboxylic acids, lower alcohols such as ethanol, propanol, etc., or mixtures thereof. Of course, a protic liquid must be chosen which does not interfere with the precipitation reaction.

If soluble salts are added as such, they will dissolve in the reaction mixture. They will subsequently be precipitated with the Group VIB metal. Within the context of this description soluble means soluble in the solvent at the temperature and pH of the reaction mixture. Suitable nickel, iron and cobalt salts which are soluble in water are nitrates, hydrated nitrates, chlorides, hydrated chlorides sulfates, hydrated sulfates, heteropolyanion compounds of Ni—Mo—W (soluble in boiling water), heteropoly anion compounds of Co—Mo—W (soluble in boiling water). It is also possible to add Group VIII non-noble metal-containing compounds which are not in solution at the time of addition, but where solution is effected in the reaction mixture. Examples of these compounds are metal compounds which contain so much crystal water that upon temperature increase the metal compound will dissolve in its own crystal water. Further, non-soluble metal salts may be added in suspension or as such and solution is effected in the reaction mixture. Suitable non-soluble metal salts are heteropolyanion compounds of Co—Mo—W (moderately soluble in cold water), heteropolyanion compounds of Ni—Mo—W (moderately soluble in cold water).

Suitable Group VIB metals are chromium, molybdenum, tungsten, or mixtures thereof. Suitable chromium, molybdenum, and tungsten compounds are soluble chromium, molybdenum, and tungsten salts. Said salts can be added to the reaction mixture in solution, wetted, or as such. If soluble salts are added as such, they will dissolve in the reaction mixture. They will subsequently be precipitated with the Group VIII non-noble metal. Suitable Group VIB metal salts which are soluble in water are ammonium salts such as ammonium para-, meta-, hexa-, and polytungstate, alkali metal salts, silicic acid salts of Group VIB metals such as molybdic silicic acid, molybdic silicic tungstic acid, tungstic acid, metatungstic acid, pertungstic acid, heteropolyanion compounds of Mo—P, Mo—Si, W—P, and W—Si. It is also possible to add Group VIB metal-containing compounds which are not in solution at the time of addition, but where solution is effected in the reaction mixture. Examples of these compounds are metal compounds which contain so much crystal water that upon temperature increase they will dissolve in their own metal water. Further, non-soluble metal salts may be added in suspension or as such, and solution is effected in the reaction mixture. Suitable non-soluble metals salts are heteropolyanion compounds of Co—Mo—W (moderately soluble in cold water), heteropolyanion compounds of Ni—Mo—W (moderately soluble in cold water).

As will be clear from the above, it is possible to add the Group VIII non-noble metal containing compound and the Group VIB metal-containing compound in various ways, at various temperatures and pHs, in solution, in suspension, and as such, simultaneously and sequentially. Five precipitation methods will be described in more detail:

1. Simultaneous precipitation at a constant pH, in which process a Group VIII non-noble metal containing acid salt compound is added slowly to a reaction vessel containing a protic liquid which is kept at a constant temperature, with the pH being kept constant by adding a base containing Group VIB metal-containing compound solution. The pH is set such that (at the chosen reaction temperature) precipitation occurs. The Group VIII metal-containing compound is added in solution or as such. It was found that the precipitate prepared by this method had a relatively large particle size depending on the dosing speed (with low dosing speed larger than 10 $\mu$m (as measured in the slurry with near forward scattering (Malvern)) and a large surface area of 100 m$^2$/g or more.

2. Simultaneous precipitation, in which process both the Group VIII non-noble metal-containing compound and the Group VIB metal-containing compound are added slowly and simultaneously to a reaction vessel containing protic liquid and a compound which decomposes upon temperature increase and thereby increases or decreases the pH. The temperature of the reaction vessel is kept at the decomposition temperature of said compound. In this case precipitation is effected by pH change, and the pH at the beginning of the reaction differs from the final pH after precipitation. It was found that the precipitation obtained with this method had a relatively large particle size (larger than 15 $\mu$m).

3. Precipitation, in which process the Group VIII non-noble metal-containing compound is added slowly to a reaction vessel containing Group VIB metal-containing compound dissolved in protic liquid (or vice versa) and a compound which decomposes upon temperature increase and thereby increases or decreases the pH. The temperature of the reaction vessel is kept at the decomposition temperature of said compound. In this case precipitation is effected by pH change, and the pH at the beginning of the reaction differs from the final pH after precipitation. It was found that the precipitate obtained with this method had a relatively small particle size (between 1 and 10 µm). It was further found that the amount of Group VIB metal compound which actually ended up in the precipitate was larger than in any of the other precipitation methods described above.
4. Precipitation at a constant pH, in which process the Group VIII non-noble metal-containing compounds; is added slowly to a reaction vessel containing Group VIB metal-containing compound dissolved in protic liquid or vice versa. The pH is kept such that (at the chosen reaction temperature) precipitation occurs by adding acid or base to the reaction vessel.
5. Solution of the metal compounds in their own crystal water with subsequent evaporation of the water so that precipitation occurs. In this method the Group VIII non-noble metal-containing compound and the Group VIB metal-containing compound are mixed in a reaction vessel and heated. After solution of the metals the water is evaporated, optionally under vacuums to effect precipitation.

One embodiment of the present invention pertains to a process for the preparation of a catalyst composition comprising a Group VIII non-noble metal and a Group VIB metal wherein a Group VIII non-noble metal-containing compound in solution and a Group VIB metal-containing compound in solution are reacted in a reaction mixture to obtain a precipitate, with the proviso that the precipitate is not nickel molybdate in which at least a portion but less than all of the molybdenum is replaced by tungsten.

Subsequently to precipitation, the precipitate may be isolated from the liquid and dried. All conventional isolation methods such as filtration, centrifugation, decantation may be used. Also all conventional drying methods are suitable such as oven drying, spray-drying, etc. The precipitate can also be dried at room temperature.

Optionally, the precipitate is thermally treated in oxygen-containing atmosphere such as air, steam, in steam and oxygen-containing atmosphere or in inert atmosphere. Said thermal treatment is conducted at a temperature between 100–600° C., preferably between 350–500° C.

In a further embodiment of the solution method of the present invention a filler is added to the reaction mixture and/or precipitate. Fillers may be added to the catalyst composition to dilute the catalyst when it is too active or to adjust the density. These fillers can be added either in suspension or as such at any stage of the process and combined with any other component added. Suitable fillers include used hydroprocessing catalyst, regenerated hydroprocessing catalysts, fresh hydroprocessing catalyst, clay, and mixtures thereof.

The precursor compound can also be readily prepared by one of several methods, including a variation of the boiling decomposition method used by Teichner and Astier in which a tungsten compound is added to the initial mixture of a molybdenum salt, a nickel salt and ammonium hydroxide. Direct precipitation and pH controlled precipitation may also be used to prepare the precursor compound. In all cases, however, water soluble salts of nickel, molybdenum and tungsten are employed.

Preferably, the molybdenum and tungsten salts are ammonium a compounds, e.g., ammonium molybdate, ammonium metatungstate, while the nickel salt may be the nitrate or hydrated nitrates.

In the boiling decomposition method, the salts are dissolved in water to make an acidic solution, after which additional $NH_4OH$ is added to make a basic solution. The solution is then heated to boiling to drive off ammonia and form a precipitate which is filtered and dried, e.g. at 100–125° C.

In the direct precipitation method, initially, the molybdate and tungstate salts are dissolved in water, $NH_4OH$ is added to form a basic solution, and the solution is warmed. A warm, e.g., 90° C., nickel salt solution (aqueous) is slowly added to the initial solution, a precipitate is formed, the solution is hot filtered and dried. In either the boiling decomposition method or the direct precipitation method, washing of the filtrate is minimized to prevent leaching.

In general, all of the components, the Ni, Mo, W, $NH_3$, are mixed in solution together and heated to a pH<7 to form the precipitate, i.e., the precursor compound. This may be accomplished by either of two methods: (1): adding all of the components together with an excess of ammonia to dissolve the components and then heating to drive off the ammonia such that the pH<7 (heating may be at less than 100° C., preferably about 50–90° C.); or (2) adding together one or more separate solutions of each component such that the final pH is <7; in each case recovering the resulting precipitate.

In another embodiment, a binder can be added to the bulk mixed metal oxide to maintain particle integrity. The binder can be silica, alumina, silica-alumina or other materials generally known as particle binders. When utilizing a binder, the amount may range from about 1–30 wt % of the finished catalyst, preferably about 5–26 wt % of the finished catalyst.

After recovering the precursor product, regardless of preparation method, the precursor is decomposed at temperatures ranging from about 300–450° C. in a suitably inert or air atmosphere.

The decomposed precursor can be sulfided or pre-sulfided by a variety of known methods. For example, the decomposition product can be contacted with a gas comprising $H_2S$ and hydrogen, e.g., 10% $H_2S/H_2$, at elevated temperatures for a period of time sufficient to sulfide the decomposition product, usually at the point of $H_2S$ breakthrough in the exit gas. Sulfiding can also be effected, in situ, by passing a typical feedstock containing sulfur over the decomposition product.

Any hydrocarbon containing feed which also contains nitrogen may be treated with the enhanced catalysts of this invention. Thus, the HDN process with these catalysts may range from petroleum distillates to residual stocks, either virgin or cracked, to synthetic fuels such as coal oils or shale oils. The HDN process is particularly useful with feeds containing high levels of nitrogen, e.g., at least about 500 wppm total nitrogen compounds. Nitrogen removal is at least about 50%, preferably at least about 80%.

Process conditions applicable for the use of the catalysts described herein may vary widely depending on the feedstock to be treated. Thus, as the boiling point of the feed increases, the severity of the conditions will also increase. The following table serves to illustrate typical conditions for a range of feeds.

| FEED | TYPICAL BOILING RANGE° C. | TEMP. ° C. | PRESS, BAR | SPACE VELOCITY V/V/HR | $H_2$ GAS RATE SCF/B |
|---|---|---|---|---|---|
| naphtha | 25–210 | 100–370 | 10–60 | 0.5–10 | 100–2.000 |
| diesel | 170–350 | 200–400 | 15–110 | 0.5–4 | 500–6.000 |
| heavy gas oil | 325–475 | 260–430 | 15–170 | 0.3–2 | 1000–6.000 |
| lube oil | 290–550 | 200–450 | 6–210 | 0.2–5 | 100–10.000 |
| residuum | 10–50% > 575 | 340–450 | 65–1100 | 0.1–1 | 2.000–10.000 |

While the invention described herein shows enhanced activity for hydrodenitrogenation, most HDN catalysts will also show hydrodesulfurization (HDS) activity. Consequently, the catalysts and processes described herein will be useful on feeds containing both nitrogen and sulfur, and will be particularly useful on feeds high in nitrogen.

The following examples will serve to illustrate, but not limit, this invention.

EXAMPLE 1

Preparation of $NH_4$—Ni—Mo—O Phase (Boiling Decomposition as per Teichner and Astier Procedure)

In a 1 liter flask, 26.5 g ammonium molybdate (0.15 moles Mo) and 43.6 g nickel nitrate hexahydrate (0.15 moles Ni) were dissolved in 300 cc of water so that the resulting pH equaled 4.3. To this solution, a concentrated $NH_4OH$ solution was added. At first, a precipitate formed which on further addition of $NH_4OH$ dissolved to give a clear blue solution with a pH of 8.3, and additional $NH_4OH$ (~250 cc) was added until a pH of 10 was reached. The solution was heated to 90° C. for 3 h during which ammonia gas evolved and a green precipitate formed. The final pH lay between 6.8 and 7. The suspension was cooled to room temperature, filtered, washed with water and dried at 120° C. overnight. About 18.6 g of material was obtained. The sample analyzed for Ni at 26.6 wt. % and Mo at 34 wt. %. The X-ray diffraction spectra of the phase matches the pattern reported by Teichner.

EXAMPLE 2

Preparation of $NH_4$—Ni—$Mo._5W_{0.5}$—O by Boiling Decomposition

Figure 2:
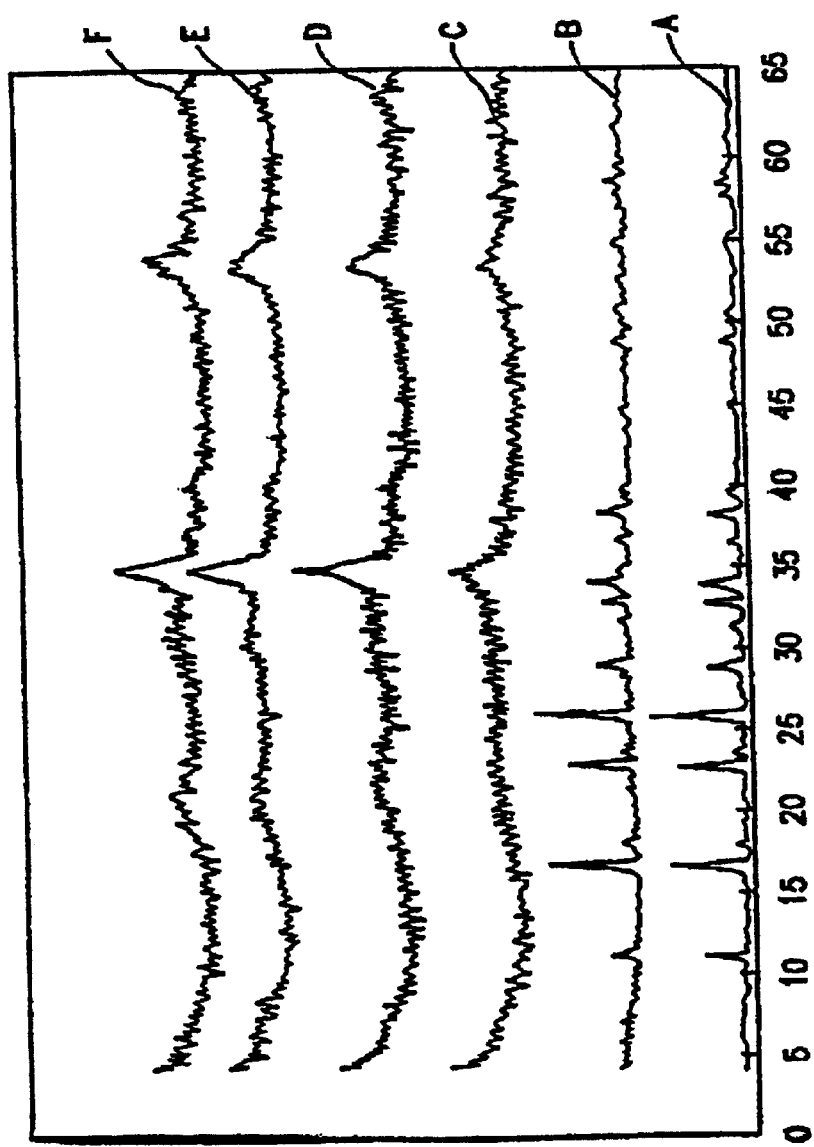
FIG. 2 shows the X-ray diffraction patterns, by CuKα radiation (λ=1.5405 Å), of $NH_4$—Ni—$Mo_{1-x}$—$W_x$—O precursors wherein curve A is $Mo_{0.9}W_{0.1}$, curve B is $Mo_{0.7}W_{0.3}$, curve C is $Mo_{0.5}W_{0.5}$, curve D is $Mo_{0.3}W_{0.7}$, curve E is $Mo_{0.1}W_{0.9}$, and curve F is $Mo_OW_1$. The ordinate and abscissa are as described for FIG. 1.

In a 1 liter flask, 13.2 g ammonium molybdate (0.075 moles Mo), 18.7 g ammonium metatungstate (0.075 moles W) and 43.6 g nickel nitrate hexahydrate (0.15 moles Ni) were dissolved in 300 cc of water so that the resulting pH equaled 4.3. To this solution, a concentrated $NH_4OH$ solution (~600 cc) was added until the pH reached 10. At this point, some precipitate remained. The solution was refluxed at ~100° C. for 3 h. During this heating, the precipitate dissolved to give a clear blue solution and on further heating, a green precipitate formed. The heating was continued until the pH reached between 6.8 and 7. The suspension was cooled to room temperature, filtered, washed with water and dried at 120° C. overnight. 18 grams of material is obtained. The X-ray diffraction spectra of the phase is given in FIG. 2 showing an amorphous background with the two largest peaks at d=2.58 and 1.70 Å.

EXAMPLE 3

Preparation of $NH_4$—Ni—$Mo_{0.5}W_{0.5}$—O by Direct Precipitation

In a 1 liter flask, 17.65 g of ammonium molybdate (0.1 mole Mo) and 24.60 g of ammonium metatungstate (0.1 mole W) were dissolved in 800 cc of water giving a solution pH of ~5.2. To this solution, 0.4 moles of $NH_4OH$ (~30 cc) was added, raising the pH to ~9.8 (solution A). This solution was warmed to 90° C. A second solution was prepared by adding 58.2 g of nickel nitrate, (0.2 moles Ni) which was dissolved in 50 cc of water (solution B) and maintained at 90° C. This solution was added dropwise at a rate of 7 cc/min into the ammonium molybdate/ammonium metatungstate solution. A precipitate begins to form after ¼ of the solution was added. This suspension which was at a pH~6.5 was stirred for 30 minutes while the temperature was maintained at 90° C. The material was filtered hot, washed with hot water, and dried at 120° C. Approximately 38 g of material was recovered.

EXAMPLE 4

Preparation of $NH_4$—Ni—$Mo_{0.5}$—$Mo_{0.5}W_{0.5}$—O by Controlled pH Precipitation Two solutions were prepared with the same amounts of nickel, tungsten, molybdenum and ammonium hydroxide are described in Example 3 (solutions A and B) except that each solution contained about 700 cc of water. The two solutions were added into a separate vessel initially containing 400 cc of water held at 90° C. Solution B (the acidic solution) was pumped into the vessel at a constant rate of ~15 cc/min, while solution A is added through a separate pump which is under feedback PC control and set to maintain the pH at 65. On mixing the two solutions a precipitate forms. The slurry was stirred at 90° C for 30 minutes, filtered hot, washed with hot water, and dried at 120° C.

EXAMPLE 5

Catalytic Evaluation Using Dibenzothiophene (DBT)

1.5–2 g of the catalysts of Examples 1–4 were placed in a quartz boat which was in turn inserted into a horizontal quartz tube and placed into a Lindberg furnace. The temperature was raised to 370° C. in about one hour with $N_2$ flowing at 50 cc/m, and the flow continued for 1.5 h at 370° C. No was switched off and 10%, $H_2S/H_2$ then added to the reactor at 20 cc/m, the temperature increased to 400° C., and held there for 2 hours. The heat was then shut off and the catalyst cooled in flowing $H_2S/H_2$ to 70° C., at which point this flow was discontinued and $N_2$ was added. At room temperature, the quartz tube was removed and the material transferred into a $N_2$ purged glove box. Catalysts were evaluated in a 300 cc modified Carberry batch reactor designed for constant hydrogen flow. The catalyst was pilled and sized to 20/40 mesh and one gram was loaded into a stainless steel basket, sandwiched between a layer of mullite beads. 100 cc of liquid feed, containing 5 wt % dibenzothiophene in decalin was added to the autoclave. A hydrogen flow of 100 cc/min was passed through the reactor and the pressure was maintained at 3150 kPa using a back pressure regulator. The temperature was raised to 350° C. at 5–6 deg/min and run until either 50% DBT was converted or until 7 hours was reached. A small aliquot of product was removed every 30 minutes and analyzed by GC. Rate constants for the overall conversion as well as the conversion to the reaction products biphenyl (BP) and cyclohexylbenzene (CHB) were calculated as described by M. Daage and R. R. Chianelli [J. Cat. 149, 414–27 (1994)] and are shown in Table 1. As described in that article, high selectivities to cyclohexylbenzene relative to BP during the desulfurization reaction are a good indication of a catalyst with high hydrodenitrogenation activity, whereas high selectivities of BP relative to CHB indicates a catalyst with high hydrodesulfurization activity.

The results show that partial substitution of tungsten for molybdenum results in catalysts that are substantially higher for DBT conversion. A standard supported Ni—Mo on $Al_2O_3$ catalyst is also shown for comparison. The high CHB/BP ratio suggests that the catalysts are active for HDN.

TABLE 1

Comparison of Activity in DBT Conversion Tests With Tungsten Addition by Different Preparation Schemes

| Catalyst | Preparation technique | Example # | $K_{total}$ @ 350° C. | CHB/BP @ 350° C. |
|---|---|---|---|---|
| $NH_4$—Ni—Mo—O | boiling decomposition | 1 | 106 | 10.4 |
| $NH_4$—Ni—$Mo_{.5}W_{.5}$—O | boiling decomposition | 2 | 171 | 10.2 |
| $NH_4$—Ni—$Mo_{.5}W_{.5}$—O | direct precipitation | 3 | 167 | 12.4 |
| $NH_4$—Ni—$Mo_{.5}W_{.5}$—O | controlled pH preparation | 4 | 181 | 12.0 |
| Ni,Mo/$Al_2O_3$ | impregnation | | 129 | 6.4 |

EXAMPLE 6

A series of catalysts were prepared in accordance with the general preparation scheme of example 2 (i.e., boiling decomposition) but varying the Mo and W relative ratios by changing the amount of ammonium molybdate and ammonium metatungstate added to the solutions. Decomposition was effected as described in Example 5. The catalysts so prepared are shown in Table 2 along with their catalytic activities for DBT measured as described in Example 5.

TABLE 2

Comparison of Activity in DBT Conversion Tests with Variation in Relative W and Mo content

| Catalyst | Sample | Ammonium molybdate (g) | Ammonium metatungstate (g) | Nickel nitrate hexahydrate (g) | $K_{total}$ @ 350° C. | CHB/BP @ 350° C. |
|---|---|---|---|---|---|---|
| $NH_4$—NiW—O | 18983-97 | 0 | 36.95 | 43.62 | 128 | 11.3 |
| $NH_4$—$NiMo_{.9}W_{.1}$—O | 18983-92 | 23.83 | 3.69 | 43.62 | 141 | 10.5 |
| $NH_4$—$NiMo_{.7}W_{.3}$—O | 18983-95 | 18.54 | 11.09 | 43.62 | 158 | 11.5 |
| $NH_4$-$NiMo_{.5}W_{.5}$—O | 18357-109 | 13.17 | 18.74 | 43.62 | 171 | 10.2 |
| $NH_4$—$NiMo_{.3}W_{.7}$—O | 18983-101 | 7.94 | 25.87 | 43.62 | 154 | 11.6 |
| $NH_4$—$NiMo_{.1}W_{.9}$—O | 18983-125 | 2.65 | 33.62 | 43.62 | 132 | 14.1 |

The data show that the most active catalyst contains an approximately equimolar mixture of tungsten and molybdenum.

EXAMPLE 7

A series of catalysts were prepared as described in Example 3 (direct precipitation) in which equimolar mixtures of Mo and W were precipitated but the nickel content was varied. Decomposition was effected as described in Example 5. The catalysts so prepared are shown in Table 3 along with their catalytic activities for DBT measured as described in example 5.

TABLE 3

Variation of Nickel Content in $NH_4$—Ni—$Mo_{.5}W_{.5}$—O Catalysts

| Catalyst | Sample | Ammonium molybdate (g) | Ammonium metatungstate (g) | Nickel nitrate hexahydrate (g) | $K_{total}$ @ 350° C. | CHB/ BP @ 350° C. |
|---|---|---|---|---|---|---|
| $NH_4$—$Ni_{0.75}Mo_{.5}W_{.5}$—O | 19086-110 | 17.65 | 24.6 | 43.65 | 171 | 13.0 |
| NH4—$Ni_{1.0}Mo_{.5}W_{.5}$—O | 19086-82 | 17.65 | 24.6 | 58.2 | 167 | 12.4 |
| $NH_4$—$Ni_{1.25}Mo_{.5}W_{.5}$—O | 19086-111 | 17.65 | 24.6 | 72.75 | 174 | 11.0 |
| NH4-$Ni_{1.5}Mo_{.5}W_{.5}$—O | 19086-112 | 17.65 | 24.6 | 87.3 | 148 | 9.55 |

Catalytic performance does not change substantially with variations in Ni from 0.75 to 1.5, although K appears to go through a maximum at about 1.25 Ni.

EXAMPLE 8

A series of catalysts were prepared in which the quantity of $NH_4OH$ used in the preparation was varied. The catalysts were prepared in accordance to the procedure described in Example 3 except that the amount of $NH_4OH$ in solution A was varied to change to $NH_4OH/Ni$ molar ratio when the two solutions were mixed. Decomposition was effected as described in Example 5. The catalysts so prepared are shown in Table 4 along with their catalytic activities for DBT measured as described in Example 5.

While decomposition of the precursor compound will drive off most, if not all, of the ammonium portion of the precursor, the preparation of the precursor and the catalytic utility of the decomposition product can be affected by the amount of $NH_4OH$ employed. Thus, the effectiveness of the decomposition product as a catalyst is enhanced when the $NH_4OH/Ni$ ratio in the preparation of the precursor compound is from about 1:1 to about 4:1, preferably about 1.5:1 to about 4:1, and more preferably about 2:1 to about 4:1. While not wishing to be bound by any particular theory or mechanism, there is some evidence the $NH_4OH/Ni$ ratio causes the Ni—M—W—O phase to change in the decomposition product.

EXAMPLE 9

The catalysts of examples 1 and 2 were compared against standard supported Ni—Mo catalysts for the conversion of a LSADO (low sulfur auto diesel oil feed). This feed contained 510 wppm sulfur, 50 wppm nitrogen, and 30.6% aromatics with a gravity of 39.8° API. The catalysts were tested at 579° F., 650 psig of $H_2$, and 1850 SCFB/B of $H_2$. The relative activities of the different catalysts are summarized in Table 5.

TABLE 5

Relative Hydrotreating Activities on LSADO Feed

| Catalyst | Relative Volumetric HDS Activity | Relative Volumetric HDN Activity |
|---|---|---|
| $Ni,Mo/Al_2O_3$ | 1 | 1 |
| $NH_4$—NiMo—O | 0.25 | 0.50 |
| $NH_4$—$Ni_{1.0}Mo_{.5}W_{.5}$—O | 1.4 | 2.05 |

TABLE 4

Variation in $NH_4OH$ Addition to Preparation

| Catalyst $NH_4OH/Ni$ mole ratio | Sample | Ammonium molybdate (g) | Ammonium metatungstate (g) | Nickel nitrate hexahydrate (g) | $cm^3$ conc $NH_4OH$ | $K_{tota}$ 1 @ 35° C. | $K_{CHB}$/ BP @ 350° C. |
|---|---|---|---|---|---|---|---|
| 1:2 | 19086-96 | 17.65 | 24.6 | 43.65 | 6.8 | 102 | 10.5 |
| 1:1 | 19086-97 | 17.65 | 24.6 | 58.2 | 14 | 137 | 10.4 |
| 2:1 | 19086-82 | 17.65 | 24.6 | 72.75 | 30 | 167 | 12.4 |
| 3:1 | 19086-104 | 17.65 | 24.6 | 87.3 | 41 | 164 | 11.4 |
| 4:1 | 19086-106 | 17.65 | 24.6 | 87.3 | 55 | 161 | 12.1 |

The Ni, $Mo/Al_2O_3$ catalyst is a standard HDN/HDS catalyst, the $NH_4$—Ni—Mo phase is the bulk phase with no tungsten, and the $NH_4$—$Ni_{1.0}Mo_{0.5}W_{0.5}$—O is the bulk phase with partial substitution of W for Mo. The $NH_4$—NiMo—O catalyst is also representative of known compounds. The catalyst of this invention is illustrated by $NH_4$—$Ni_{1.0}Mo_{0.5}W_{0.5}$—O and the data show the clear advantage of ammonium nickel tungsten molybdate for HDN activity.

EXAMPLE 10

Preparation of a Bulk Catalyst Composition According to the Solid Route 18.1 kg-ammonium dimolybdate (15.33 kg $MoO_3$) are dissolved in 575 liters water. Subsequently 28.5 kg ammonium metatungstate (24 69 kg $WO_3$) is added to the solution. The resulting solution is preheated up to 90° C. 26.5 kg $NiCO_3$ (49.7% Ni) powder is mixed with water and the resulting paste is added to the ammonium dimolybdate/ammonium metatungstate solution. The resulting mixture is reacted for 7 hours at 89° C.

EXAMPLE 11

Preparation of a Bulk Catalyst Composition According to the Solution Route

In a 1-liter flask, 13.2 g ammonium molybdate (0.075 moles Mo), 18.7 g arnmmonium.metatungstate (0.075 moles W) and 43.6 g nickel nitrate hexahydrate (0.15 moles Ni) were dissolved in 300 ml water so that the resulting pH equaled 4.3. To this solution, a concentrated $NH_4OH$ solution (about 600 ml) was added until the pH reached 10. At this point, some precipitate remained. The solution was refluxed at 100° C. for 3 hours. During this heating, the precipitate dissolved to give a clear blue solution and on further heating, a green precipitate formed. The heating was continued until the pH reached a value between 6.8 and 7.0. The suspension was cooled to room temperature, filtered, washed with water and dried at 120° C. overnight. 18 grams of material were obtained.

EXAMPLE 12

Sample 2110587

657 g of a NiMo—W bulk catalyst composition obtained according to the procedure described in Examples 10 or 11 was added to 1362 g of an aqueous slurry containing 125 g of alumina (prepared by precipitation of sodium aluminate and aluminum sulfate). The resulting Ni—Mo—W bulk catalyst—alumina composition was subsequently mixed at 80° C. until an LOI of 31% was obtained. The resulting composition was subsequently extruded and the extrudates were dried at 120. C. for about 90 minutes and subsequently calcined at 385° C. for one hour in air.

EXAMPLE 13

Sample 2110598

The process of Example 12 was repeated except mat instead of the alumina suspension, a silica sol containing 10 wt. % silica were applied.

EXAMPLE 14

Sample 2110591

657 g of a Ni—Mo—W bulk catalyst composition obtained according to the procedure described in Examples 7 or 8 was added to 510 g of a boehmite paste containing 125 g boehmite. The rebuffing paste was mixed at 60° C. to obtain an LOI of 42%. The resulting composition was extruded, dried and calcined as described in Example 12.

EXAMPLE 15

Sample 2110469

The procedure described In Example 7 or 8 was repeated except that alumina is present during the preparation of the bulk catalyst composition. To 755 g of the resulting dried Ni—Mo—W bulk catalyst-alumina composition containing 60 g alumina, 461 g water and a small amount of nitric acid were added. The resulting mixture was mixed at 70° C. while evaporating water until an LOI of 34% was obtained. The resulting composition was extruded, dried and calcined as described in Example 12.

EXAMPLE 16

Ammonium molybdate, ammonium tungsten and/or ammonium chromate are dissolved and combined in a first reactor. The temperature is increased to 90° C. The Group VIII salt is dissolved in a second reactor and heated to 90° C. Ammonium hydroxide is added to the first reactor to form a basic solution. The Group VIII metal solution is added to the first dropwise with stirring in 20 minutes. After 30 minutes, the precipitate is filtered and washed. The precipitate is dried overnight at 120° C. and calcined at 385° C.

EXAMPLE 17

The precipitation method of Example 16 was used to prepare a precipitate from ammonium dimolybdate, ammonium meta tungstate and $Fe(III(NO_3)_3.9\ H_2O$ in 98% yield comprising 41.2 wt. % $Fe_2O_3$, 21.3 wt. % $MoO_3$, and 36.9 wt. % $WO_3$. The surface area of the precipitate was 76 $m^2/g$. The pore volume as measured up to 60 nm by BET using the adsorption curve was 0.147 ml/g.

EXAMPLE 18

The precipitation method of Example 16 was used to prepare a precipitate from $Ni(CO_3)_2.6H_2O$, $(NH_4)_2MO_7O_{24}.4H_2O$, and $(NH_4)_2Cr_2O_7$ in 87.7% yield comprising 52.2 wt. % NiO, 29.4 wt. % $MoO_3$, and 16.6 wt. % $Cr_2O_3$. The surface area of the precipitate was 199 $m^2/g$. The pore volume as measured up to 60 nm by BET using the adsorption curve was 0.276 ml/g.

EXAMPLE 19

The precipitation method of Example 16 was used to prepare a precipitate from $Ni(CO_3)_2.6H_2O$, $(NH_4)_6H_2W_{12}O_{40}$, and $(NH_4)_2Cr_2O_7$ in 87.7% yield comprising 44.0 wt. % NiO, 42.4 wt. % $WO_3$, and 11.8 wt. % $Cr_2O_3$. The surface area of the precipitate was 199 $m^2/g$. The pore volume as measured up to 60 nm by BET using the adsorption curve was 0.245 ml/g.

EXAMPLE 20

A 350N dewaxed oil was processed at hydrotreating conditions in a small scale pilot unit over both a conventional NiMo hydrotreating (HT) catalyst and the bulk metal catalyst. Feed quality, operating conditions and pilot plant test results are given in the table below. The extent of saturation over the bulk metal catalyst is much higher, even at milder operating conditions, than for the conventional HT catalyst. The relative desulfurization activity for the bulk metal catalyst was about 600% higher than the conventional catalyst.

|  | 350N Dewaxed Oil Feed | Conventional NiMo HT Catalyst | | Bulk Metal Catalyst | |
|---|---|---|---|---|---|
| H2 Partial Pressure, psig |  | 2000 | 2000 | 2000 | 2000 |
| H2 Treat Gas Rate, SCF/bbl |  | 2500 | 2500 | 2500 | 2500 |
| RX Temp, ° C. |  | 350 | 340 | 300 | 325 |
| RX LHSV, hr-1 |  | 0.6 | 1.7 | 0.6 | 1.6 |
| Dewaxed 390C+ Product Properties |  |  |  |  |  |
| UV Absorbance at 274 nm | 650 | 72.5 | 162 | 9.2 | 237 |
| Saturates, wt % | 76.7 | 91.7 | 89.2 | 93.4 | 93 |
| Sulfur, wppm | 238 | 0.9 | 14 | 1.3 | 1.2 |

EXAMPLE 21

A 350N dewaxed oil was processed at hydrotreating conditions in a small scale pilot unit over conventional NiMo hydrotreating (HT) catalyst followed by a bulk metal catalyst. H2S and NH3 were removed from the treat gas between catalysts. Feed quality, operating conditions and pilot plant test results are given in the table below. Very low levels of sulfur and UV absorbance were achieved.

|  | 350N Dewaxed Oil Feed | R1 Conventional NiMo HT Catalyst | R2 Bulk Metal Catalyst |
|---|---|---|---|
| H2 Partial Pressure, psig |  | 2000 | 2000 |
| H2 Treat Gas Rate, SCF/bbl |  | 2500 | 2500 |
| RX Temp, ° C. |  | 330 to 350 | 325 |
| RX LHSV, hr-1 |  | 0.6 to 2.0 | 1.8 |
| Dewaxed 390C+ Product Properties |  |  |  |
| UV Absorbance at 274 nm | 650 | 93.4 | 14.5 |
| Saturates, wt % | 76.7 | 91.1 | 93.3 |
| Sulfur, wppm | 238 | 0.9 | 0.5 |

What is claimed is:

1. A process for preparing a lubricating oil basestock containing at least about 90% saturates which comprises:
   (a) passing a feedstock to a hydrotreating zone containing at least one hydrotreating reactor containing a hydrotreating catalyst;
   (b) hydrotreating the feedstock in the presence of the hydrotreating catalyst under hydrotreating conditions wherein the hydrotreating catalyst comprises a bulk metal catalyst represented by the formula:

$(X)_b(Mo)_c(W)_d O_z$ wherein X is non-noble Group VIII metal, and the molar ratio of b: (c+d) is 0.5/1 to 3/1 to produce a hydrotreated feedstock; and
   (c) fractionating the hydrotreated feedstock.

2. A process for preparing a lubricating oil basestock containing at least about 90% saturates which comprises:
   (a) passing a feedstock to a first hydrotreating zone containing at least one hydrotreating reactor containing a first non-bulk metal hydrotreating catalyst;
   (b) hydrotreating the feedstock in the presence of the first hydrotreating catalyst under first hydrotreating conditions wherein the first hydrotreating catalyst comprises at least one Group VIB and at least one non-noble Group VIII metal on a refractory oxide support to produce a first hydrotreated feedstock;
   (c) passing at least a portion of the first hydrotreated feedstock to a second hydrotreating zone containing at least one hydrotreating reactor containing a second hydrotreating catalyst;
   (d) hydrotreating the first hydrotreated feedstock in the second hydrotreating zone under second hydrotreating conditions wherein the second hydrotreating catalyst in said second hydrotreating zone comprises a bulk metal catalyst represented by the formula:

$(X)_b(Mo)_c(W)_d O_z$ wherein X is non-noble Group VIII metal, and the molar ratio of b: (c+d) is 0.5/1 to 3/1 to produce a hydrotreated feedstock; and
   (e) fractionating the second hydrotreated feedstock.

3. A process for preparing a petroleum oil containing at least about 90% saturates which comprises:
   (a) passing a feedstock to a hydrotreating zone containing at least one hydrotreating reactor containing a hydrotreating catalyst;
   (b) hydrotreating the feedstock in the presence of the hydrotreating catalyst under hydrotreating conditions wherein the hydrotreating catalyst is a bulk metal catalyst represented by the formula:

$(X)_b(Mo)_c(W)_d O_z$ wherein X is non-noble Group VIII metal, and the molar ratio of b: (c+d) is 0.5/1 to 3/1 to produce a hydrotreated feedstock;
   (c) fractionating the hydrotreated feedstock to produce a first basestock;
   (d) passing the first basestock to a hydrogenation zone containing at least one hydrogenation reactor containing a hydrogenation catalyst:
   (e) hydrogenating the first basestock in the presence of the hydrogenation catalyst under hydrogenation conditions wherein the hydrogenation catalyst comprises at least one Group VIII metal; and
   (f) fractionating the hydrogenated product from step (e) to produce a petroleum oil containing at least about 90% saturates.

4. The process of claims 1, 2 or 3 wherein the molar ratio of c:d is >0.01, and z=[2b+6(c+d)]/2.

5. The processes of claims 1, 2 or 3 wherein the molar ratio of b:(c+d) is 0.75/1 to 1.5/1.

6. The process of claim 5 wherein the molar ratio of b:(c+d) is 0.75/1 to 1.25/1.

7. The process of claim 4 wherein the molar ratio of c:d is >0.1/1.

8. The process of claim 7 wherein the molar ratio of c:d is 1/10 to 10/1.

9. The process of claim 8 wherein the molar ratio of c:d is 1/3 to 3/1.

10. The process of claim 3 wherein the hydrogenation catalyst further contains at least one Group VIB metal.

11. The process of claim 3 wherein the Group VIII metal is a non-noble metal.

12. The process of claim 11 wherein the non-noble metal is nickel.

13. The process of claims 1 or 3 wherein the hydrotreating conditions comprise temperatures of from 250 to 400° C., hydrogen pressures of from 500 to 3500 psig (3549 to 24234 kPa), liquid hourly space velocities of from 0.1 to 5.0 and hydrogen treat gas rates of from 500 to 5000 scf/B (89 to 890 m$^3$/m$^3$).

14. The process of claim 2 wherein the first hydrotreating conditions in the first hydrotreating zone comprise temperatures of from 250 to 400° C., hydrogen pressures of from 500 to 3500 psig (3549 to 24234 kPa), liquid hourly space velocities of from 0.1 to 5.0 and hydrogen treat gas rates of from 500 to 5000 scf/B (89 to 890 m$^3$/m$^3$), and the second hydrotreating conditions in the second hydrotreating zone comprise temperatures of from 250 to 400° C., hydrogen pressures of from 500 to 5000 psig (3549 to 24234 kPa), liquid hourly space velocities of from 0.1 to 5.0 and hydrogen treat gas rates of from 500 to 5000 scf/B (89 to 890 m$^3$/m$^3$).

15. The process of claim 3 wherein the hydrogenation conditions comprise temperatures of from 150 to 400° C., hydrogen pressures of from 500 to 3500 psig (3549 to 24234 kPa), liquid hourly space velocities of from 0.1 to 5.0 and hydrogen treat gas rates of from 500 to 5000 scf/B (89 to 890 m$^3$/m$^3$).

16. The process of claim 3 wherein the petroleum oil is a white oil.

17. The process of claim 16 wherein the white oil is a technical or medicinal white oil.

18. The process of claim 4 wherein the non-noble metal is Ni or Co.

19. The process of claim 4 wherein the non-noble metal is Ni.

20. The process of claims 1 or 2 wherein the lubricating oil is a white oil.

* * * * *